US009512396B2

(12) United States Patent
Chen et al.

(10) Patent No.: US 9,512,396 B2
(45) Date of Patent: Dec. 6, 2016

(54) IN VITRO MICROPHYSIOLOGICAL SYSTEM FOR HIGH THROUGHPUT 3D TISSUE ORGANIZATION AND BIOLOGICAL FUNCTION

(71) Applicant: The Trustees of the University of Pennsylvania, Philadelphia, PA (US)

(72) Inventors: Christopher S. Chen, Princeton, NJ (US); Ken Margulies, Villanova, PA (US); Thomas Boudou, Philadelphia, PA (US); Wesley Legant, Philadelphia, PA (US); Michael T. Yang, Philadelphia, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 56 days.

(21) Appl. No.: 14/247,951

(22) Filed: Apr. 8, 2014

(65) Prior Publication Data
US 2014/0220555 A1 Aug. 7, 2014

Related U.S. Application Data

(63) Continuation of application No. PCT/US2012/059910, filed on Oct. 12, 2012.

(60) Provisional application No. 61/593,043, filed on Jan. 31, 2012, provisional application No. 61/546,427, filed on Oct. 12, 2011.

(51) Int. Cl.
| | |
|---|---|
| *C12Q 1/02* | (2006.01) |
| *C12N 5/00* | (2006.01) |
| *C12N 5/077* | (2010.01) |
| *C12M 3/00* | (2006.01) |
| *C12M 1/32* | (2006.01) |
| *C12M 1/34* | (2006.01) |
| *C12N 1/14* | (2006.01) |
| *C12N 1/20* | (2006.01) |
| *C12N 7/00* | (2006.01) |
| *C12Q 1/68* | (2006.01) |
| *G01N 33/50* | (2006.01) |

(52) U.S. Cl.
CPC ............ *C12N 5/0062* (2013.01); *C12M 21/08* (2013.01); *C12M 23/12* (2013.01); *C12M 41/36* (2013.01); *C12N 1/14* (2013.01); *C12N 1/20* (2013.01); *C12N 5/0657* (2013.01); *C12N 7/00* (2013.01); *C12Q 1/025* (2013.01); *C12Q 1/68* (2013.01); *G01N 33/5005* (2013.01); *C12N 2527/00* (2013.01)

(58) Field of Classification Search
CPC ... C12N 5/0062; C12N 2527/00; C12N 5/067; G01N 33/005; C12M 23/12; C12Q 1/025
See application file for complete search history.

(56) References Cited

FOREIGN PATENT DOCUMENTS

| WO | WO 2007/087402 A2 | 8/2007 |
| WO | WO 2008/114204 A2 | 9/2008 |

OTHER PUBLICATIONS

Boudou et al., A microfabricated platform to measure and manipulate the mechanics of engineered cardiac microtissues. Tissue Engineering, vol. 18, No. 9 and 10 (online Nov. 17, 2011) pp. 910-919.*
Tanaka et al., In vitro pharmacologic testing using human induced pluripotent stem cell-derived cardiomyocytes. Biochemical and Biophysical Research Communications, vol. 385, No. 4 (Aug. 7, 2009) pp. 497-502.*
Akera et al., "Correlation of Cardiac Sodium- and Potassium-Activated Adenosine Triphosphatase Activity with Ouabain-Induced Inotropic Stimulation", *J. Pharmacol. Exp. Ther.*, 173(1):145-151 (1970).
Borzak et al., "Mechanisms of Rate Staircase in Rat Ventricular Cells", *Am. J. Physiol. Heart Circ. Physiol.*, 260(3 Pt 2):H884-H892 (1991).
Carrier et al., "Cardiac Tissue Engineering: Cell Seeding, Cultivation Parameters, and Tissue Construct Characterization", *Biotechnol. Bioeng.*, 64(5):580-589 (1999).
Eschegan et al., "Engineering Myorcardial Tissue", *Circ. Res.*, 97(12):1220-1231 (2005).
Gadsby et al., "Voltage Dependence of Na/K Pump Current in Isolated Heart Cells", *Nature*, 315(6014):63-65 (1985).
Kattman et al., "Stage-Specific Optimization of Activin/Nodal and BMP Signaling Promotes Cardiac Differentiation of Mouse and Human Pluripotent Stem Cell Lines", *Cell Stem Cell*, 8(2):228-240 (2001).
Kofidis et al., "In Vitro Engineering of Heart Muscle: Artificial Myorcardial Tissue", *J. Thorac. Cardio. Sur.*, 124(1):63-69 (2002).
Leon et al., "Positive Inotropic Stimulation", *Current Opin. Crit. Care*, 8(5):395-403 (2002).
Mathers et al., "Global Burden of Disease: Data Sources, Methods and Results", *World Health Organization*, Table of Contents, (2004).
Niebruegge et al., "Generation of Human Embryonic Stem Cell-Derived Mesoderm and Cardiac Cells Using Size-Specified Aggregates in an Oxygen-Controlled Bioreactor", *Biotechnol. Bioeng.*, 102(2):493-507 (2009).

(Continued)

*Primary Examiner* — Kara Johnson
(74) *Attorney, Agent, or Firm* — Baker Botts L.L.P.

(57) ABSTRACT

Techniques for generating microtissues, including a microfabricated platform including at least one micro-well including a plurality of micro-cantilevers coupled thereto and surrounded by a plurality of ridges, each micro-cantilever including a cap at a terminal end thereof. The platform can be immersed in a suspension of cells. The suspension of cells can be driven into at least one micro-well, and the ridges can be de-wetted to remove excess suspension and isolate the suspension of cells in each micro-well. The cells can be driven in the suspension of each micro-well toward a top surface of the suspension, which can be polymerized to form a matrix. The cells can be cultivated to spontaneously compact the matrix such that the micro-cantilevers anchor and constrain the contracting matrix to form a band of microtissue that spans across the micro-cantilevers.

45 Claims, 18 Drawing Sheets

(56) References Cited

OTHER PUBLICATIONS

Sage et al., "Automatic Tracking of Individual fluorescence Particles: Application to the Study of Chromosome Dynamics", *IEEE Transactions on Image Processing*, 14(9):1372-1383 (2005).

Samuel et al., "Mechanically Induced Orientation of Adult Rat Cardiac Myocytes in Vitro", *in Vitro Cell Dev. Biol.*, 26(9):905-914 (1990).

Schouten et al., "Role of ICA and Na+ca+ Exchange in the Force-Frequency Relationship of Rat Heart Muscle", *J. Mol. Cell Cardiol.*, 23(9):1039-1050 (1991).

Shapira-Schweitzer et al., "Matrix Stiffness Affects Spontaneous Contraction of Cardiomyocytes Cultured Within a PEGylated Fibrinogen Biomaterial", *Acta Biomaterials. A.*, 3(1):33-41 (2007).

Smotherman et al., "Heart Rate Response of the Rat Fetus and Neonate to a Chemosensory Stimulus", *Physiology & Behavior*, 50(1):47-52 (1991).

Tang et al., "Force-Frequency Response in Isoproterenol-Induced Hypertrophied Rat Heart", *Eur. J. Pharmacol.*, 318(2-3):349-356 (1996).

van Luyn et al., "Cardiac Tissue Engineering: Characteristics of in Unison Contracting Two- and Three-Dimensional Neonatal Rat Ventricle Cell (co)-Cultures", *Biomaterials*, 23(24):4793-4801 (2002).

Zimmerman et al., "Embryonic and Embryonic-Like Stem Cells in Heart Muscle Engineering", *J. Mol. Cell Cardiol.*, 50(2):320-326 (2011).

Zimmerman et al., "Engineered Heart Tissue Grafts Improve Systolic and Diastolic Function in Infarcted Rat Hearts", *Nat. Med.*, 12(4):452-458 (2006).

Zimmerman et al., "Three-Dimensional Engineered Heart Tissue from Neonatal Rat Cardiac Myocytes", *Biotechnol. Bioeng.*, 68(1):106-114 (2000).

Deepak, Choudhury, et al., "Exploitation of physical and chemical constraints for three-dimensional microtissue construction in microfluidics", *Biomicrofluidics*, vol. 5, No. 2, Jan. 1, 2011, p. 022203, XP055162586, ISSN: 1932-1058.

Radisic, M., et al., "High-Density seeding of myocyte cells for cardiac tissue engineering", *Biotechnology and Bioengineering*, Wiley & Sons, Hoboken, NJ, US, vol. 82, No. 4, May 20, 2003, pp. 403-414, XP002587856, ISSN: 0006-3592.

Tan, J. L., et al., "Cells lying on a bed of microneedles: An approach to isolate mechanical force", *Proceedings of the National Academy of Sciences, National Academy of Science*, US, vol. 100, No. 4, Feb. 18, 2003, pp. 1484-1489, XP002319115, ISSN: 0027-8424.

W.R. Legant, et al., "Microfabricated tissue gauges to measure and manipulate forces from 3D microtissues", *Proceedings of the National Academy of Sciences*, vol. 106, No. 25, Jun. 23, 2009, pp. 10097-10102, XP055149619, ISSN: 0027-8424.

Extended European Search Report dated Feb. 5, 2015 in EP Application No. 12839742.9.

\* cited by examiner

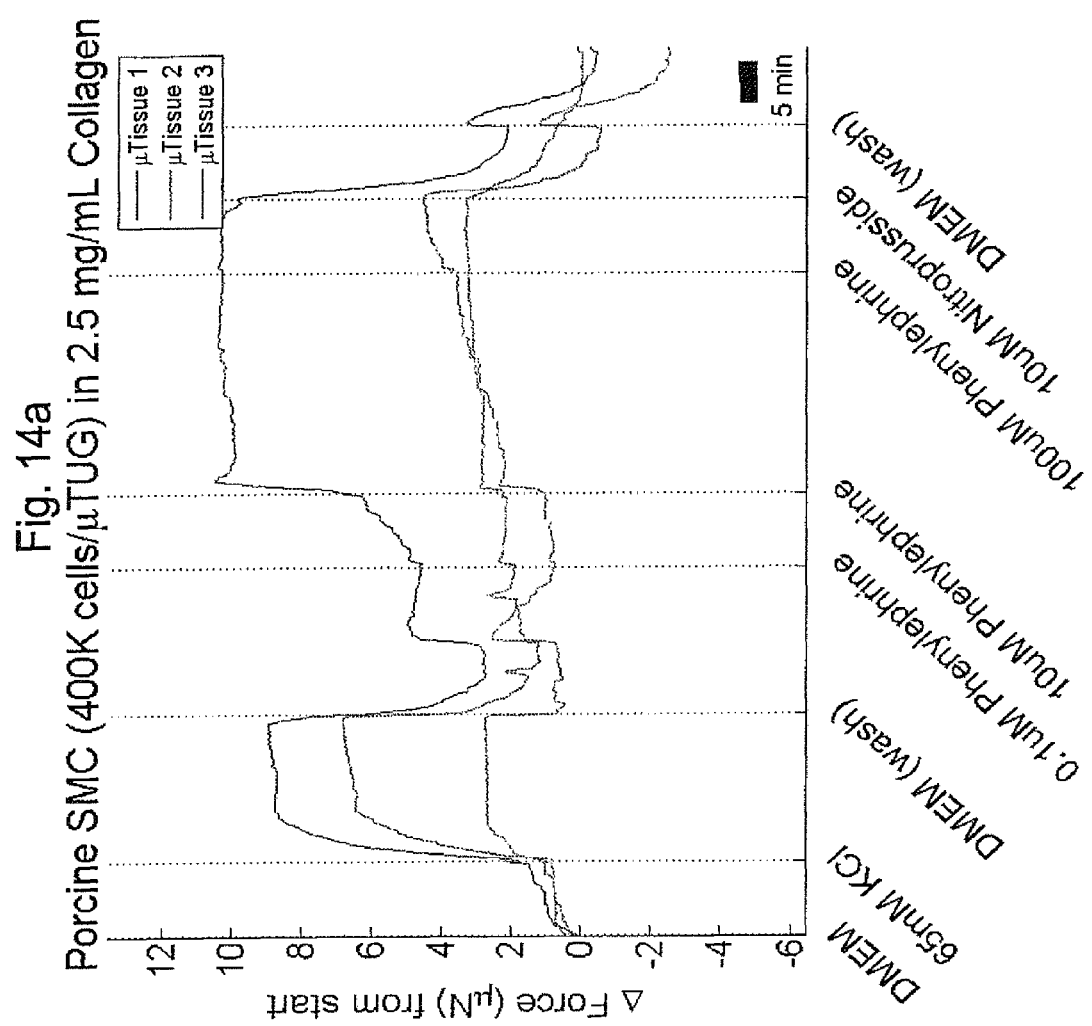

IN VITRO MICROPHYSIOLOGICAL SYSTEM FOR HIGH THROUGHPUT 3D TISSUE ORGANIZATION AND BIOLOGICAL FUNCTION

CROSS-REFERENCE TO RELATED APPLICATIONS

This application is a continuation of PCT/US12/059910, filed Oct. 12, 2012, which claims priority to both of U.S. Provisional Ser. No. 61/593,043, filed on Jan. 31, 2012, and U.S. Provisional Application No. 61/546,427, filed Oct. 12, 2011, all three of which is incorporated herein by reference its entirety.

STATEMENT OF FEDERALLY SPONSORED RESEARCH OR DEVELOPMENT

This invention was made with government support under grants EB00262 and EB08396, awarded by the National Institute of Biomedical Imaging and Bioengineering, and HL73305 and HL90747, awarded by National Heart, Lung, Blood Institute The government has certain rights in the invention.

BACKGROUND

The disclosed subject matter provides techniques for the generation of microtissues within three-dimensional constructs for uses including screening applications.

Heart failure imposes a major public health burden that is inadequately addressed by current approaches, striking one of every five Americans and accounts annually for approximately one million hospitalizations, over 50,000 deaths, and almost $35 billion in health care costs.

One approach to understanding the pathogenesis of heart failure can include using manipulating individual genes in animal models. Certain research in this area has implicated a variety of individual molecules, signaling pathways and gene programs in the myocardial response to injury and overload. Despite these preclinical advances, few of these regulators have been rigorously assessed in the human heart, and translation into an effective heart failure therapy remains merely an aspiration—pharmacologic therapy for heart failure has changed little over the past 15 years. Contributors to this "translational divide" in agents targeting the heart may include, for example, shortcomings of existing animal models and the absence of suitable in vitro models that reflect the biology of the human myocardium.

Although human induced pluripotent stem cell (iPSC) derived myocytes have demonstrated patient-specific electrophysiological abnormalities (e.g., action potential prolongation in myocytes from patients with the long-QT syndrome due to KCNQ1 mutation), iPSC-derived myocytes can fail to recapitulate certain of the critical functions of tissue when they are cultured using traditional 2D culture substrates. The adhesion of cells to a rigid, planar substrate can be structurally and mechanically non-physiologic. For example, cells can assume a flattened morphology with an artificial introduction of apical-basal polarity of cell-matrix adhesions, and cell-cell adhesions can be unable to bear substantial mechanical load owing to the rigid constraint of the underlying substrate. As a result, the architecture of these cells can differ from those of in vivo tissue. Thus, certain aspects of physiology and pathology involving contractile and structural responses can be unmet by traditional 2D approaches.

Characteristic physiological and pathological responses to biomechanical load, transduced through complex three-dimensional tissue architecture, are fundamental features of the myocardium. Variations in preload and afterload can alter myocardial contractility on a beat-to-beat basis and induce changes in myocardial gene expression and growth over time. Conversely, the absence of relevant biomechanical cues or a multicellular, three-dimensional (3D) architecture can distort the phenotype of in vitro myocardial models. Thus, myocytes adapted to conventional two-dimensional cell culture models can differ from those of freshly isolated myocytes from the intact heart. Developmental and species differences can further exacerbate differences between adult human myocardium and conventionally used neonatal rodent myocyte cultures. Together, these realities can compromise the clinical relevance of efforts to use cultured myocyte models in basic, translational and preclinical pharmacological research.

Additionally, these issues are not limited to cardiac testing, as many other tissues and biological processes are faced with similar concern, such as high cost, ethical concerns, and experimental limitations of animal models. For example, certain techniques used in connection with other tissues can likewise fail to recapitulate biological functions of the tissues. The use of stem cell technologies can produce useful sources of human cells. These cells can, in some cases, regain certain in vivo functions in an appropriate in vitro environment. However, certain techniques for generating tissues from these cells in an in vitro environment can fail to provide clinically relevant culture models.

Accordingly, there is a need for improved techniques for the generation of microtissues, including cardiac microtissues.

SUMMARY

The disclosed subject matter provides techniques for generating microtissues includes providing a micro-fabricated platform including at least one micro-well surrounded by a plurality of ridges. In an exemplary method, a plurality of micro-cantilevers can be coupled to a bottom surface of the micro-well, and each micro-cantilever can include a cap at a terminal end thereof. The platform can be immersed in a suspension of cells, and the suspension can be driven into the micro-well. The ridges can be de-wetted to remove excess suspension, which can isolate the suspension of cells in each micro-well. The cells in the suspension can be driven toward a top surface of the suspension. The suspension can then be polymerized to form a matrix, and the cells can be cultivate over time to spontaneously compact the matrix. The micro-cantilevers can anchor the contracting matrix, and can constrain the contraction of the matrix to form a band of microtissue that spans across the micro-cantilevers.

In certain embodiments, the suspension of cells can include a reconstitution mixture or prepolymer, such as collagen and fibrinogen. The cells can include any adherent cells, including neonatal rat heart cells, human cells, human iPSC-derived cardiomyocytes. The cells can include one or more of heart cells, muscle cells, liver cells, neural cells, mesodermal, ectodermal, or endodermal lineage, embryonic or adult stem cells, fibroblasts, endothelial cells, smooth muscle cells of any origin, skeletal muscle cells, cardiac myocytes, myofibroblasts, epithelial cells, neuronal cells, glial cells, astrocytes, hepatocytes, kidney epithelial cells, intestinal cells, lymphocytes, or leukocytes. Additionally or alternatively, the cells can include one or more of cells of human origin or cells of non-human origin including mouse cells, rat cells, rabbit cells, pig cells, bovine cells, primate cells, non-mammalian cells, fish cells, insect cells, mold cells, dictostelium cells, worm cells, or *drosophila* cells. Moreover, the cells can include one or more of cancer cells, non-eukaryotic cells, bacteria, or viruses.

The micro-fabricated platform can include a plurality of micro-wells. In certain embodiments, at least a first of the plurality of micro-wells can include cells from a first patient, and at least a second of the plurality of micro-wells include cells from a second patient. At least a first of the plurality of micro-wells can include diseased cells and at least a second of the plurality of cells can include normal cells. At least one micro-well can include a first cell type and a second micro-well can include a second cell type, and a difference in a viability metric between the first and second cell types can be identified. In certain embodiments, the method can further include electrically stimulating the bands and microtissue to synchronize beating, if any, of the band of microtissues.

In certain embodiments, the method can further include measuring a contractile function of the band of microtissue. The micro-fabricated platform can be imaged, over time, to acquire image data. A force exerted on the micro-cantilevers can be determined based on at least the image data and a spring constant corresponding to each micro-cantilever. A contractile function can be identified based on at least the determined force. Additionally, each cap of each micro-cantilever can include one or more fluorescent emitters. Imaging the micro-fabricated platform can include imaging the fluorescent response of the fluorescent emitters. A static force and dynamic force exerted on the micro-cantilevers can be measured, over time, based on at least the determined force, over time. In certain embodiments, the contractile function can include one or more of beat frequency, contraction duration, change in beat frequency over time, change in contraction duration over time, peak force, mean force, minimum force, change in force over time, variance in any of these parameters, and/or ratio of peak force to base force. A structural characterization of the band of microtissue can be measured, such as alpha-actinin periodicity, cell alignment, or multicellular organization.

In certain embodiments, the method can further include identifying a compound that modulates the contractile function of the band of microtissue. The compound can be introduced to the band of microtissue in one of the plurality of micro-wells. A difference between the identified contractile function of the band of microtissue introduced to the compound can be detected relative to a band of microtissue of another of the micro-wells. The compound can be a pharmacologic agent. Additionally or alternatively, the compound can be one or more of a small-molecule pharmaceutical, a biologic, a siRNA, a bodily fluid, and organic compound, or an inorganic compound.

The method can also include determining an effect of a compound on the contractile function of the band of microtissue. The compound can be introduced to the microtissue of one of the plurality of micro-wells, and the effect on contractile function of the compound relative to a microtissue of another micro-well can be determined. For example, one micro-well can include a band of microtissue of a first patient, and a second micro-well can include a band of microtissue of a second patient, and the effect of a compound on the tissue of the first patient can be determined relative of the effect of the compound on the second patient. Moreover, the method can include determining an effect of an environmental factor, such as gravity, hypoxia, pressure, magnetic field, smoke, or the presence of nanoparticles, on the contractile function of the band of microtissue.

In certain embodiments, the method can further include measuring the level of calcium within the microtissue. One or more fluorescent dies can be introduced into the microtissue, and the fluorescent response of the fluorescent dies can be imaged, over time. The fluorescent response can correspond to a calcium concentration within the microtissue. An electrical characteristic of the microtissue can be determined based on at least the calcium concentration, over time. For example, a delay between release of calcium within the microtissue and the dynamic forces exerted by the microtissue can be determined.

The disclose subject matter also provides systems for generating microtissues, which includes a micro-fabricated platform including at least one micro-well with a plurality of micro-cantilevers coupled to the micro-well. Each micro-well can be surrounded by a plurality of ridges, and each micro-cantilever can have a cap at its terminal end. A centrifuge can be coupled to the platform for driving a suspension of cells into the at least one micro-well, and for driving cells in the suspension of each micro-well toward a top surface of the suspension. An incubator can be coupled to the platform for polymerization of the suspension of cells and for providing for the maturation of the cells into a band of microtissue that spans across the micro-cantilevers. An imaging device can be arranged to optically image the platform, and can be configured for imaging at least a displacement of the plurality of micro-cantilevers over time. A processor can be coupled to the imaging device for determining a displacement of the micro-cantilevers, over time, and for determining a force exerted by the band of microtissue on the micro-cantilevers based on the displacement of the micro-cantilevers over time.

In one embodiment, the system can further include an electrode place on each side of the micro-fabricated platform. The electrodes can be coupled to a voltage control circuit adapted to apply electrical stimulation at a predetermined frequency. The micro-fabricated platform can be formed from PDMS, rubber, one or more polycaprolactones, one or more polyurethanes or one or more hydrogels including hydrogels formed from polyacrylamide or polyethylene glycol. Each cap of each micro-cantilever can include one ore more fluorescent emitters, and the imaging device can be further adapted to detect a fluorescent response from the fluorescent emitters.

In certain embodiments, the micro-fabricated platform can include a well plate including one or more micro-wells. Each well can include at least one of the micro-wells, and each micro-well can be separated by a plurality of ridges. Each well can include one to three micro-wells, and each ridge can separate the micro-wells by approximately 100 microns. In certain embodiments, the well plate can include a gasket layer bonded to a substrate layer. The gasket layer can have one or more holes with a conical wall profile, and the gasket layer can be arranged such that each hole is aligned over one or more micro-wells, each hole thereby forming a well. In certain embodiments, the micro-fabricated platform can include a large format well including an array of ten by thirteen micro-wells spaced approximately 800 microns apart. The array can cover a surface area of approximately 1.9 cm by 1.9 cm.

The disclosed subject matter also provides a device for assessing the biomechanical functioning of microtissues. The device can include a micro-fabricated platform including at least one micro-well formed therein. The boundaries of each micro-well defined by a plurality of ridges. A plurality of micro-cantilevers can be coupled to a bottom surface of each micro-well, and a cap can be coupled to the terminal end of each micro-cantilever. A band of microtissue can span across each micro-cantilever. The micro-fabricated platform and the at least one micro-well formed therein can be adapted to receive a suspension of cells and the plurality of micro-cantilevers can be adapted to anchor a matrix formed from the suspension of cells as the matrix spontaneously compacts, over time, and to constrain the contraction of the matrix to form the band of microtissue spanning across the micro-cantilevers.

Each micro-well can be a rectangular micro-well with rounded corners and dimensions of 800 μm by 800 μm by 400 μm. Each micro-cantilever can be between 35 μm and 80 μm thick and less than 140 μm tall. Each micro-cantilever can be 45 μm thick, 100 μm wide, and 140 μm tall. The device can be further adapted to provide for measurement of deflections of the micro-cantilevers of between 0.1 μm and 50 μm, and wherein the spring constant of each micro-cantilever is between 0.2 μN/μm and 0.45 μN/μm. Where the spring constant of each micro-cantilever is 0.45 μN/μm, the device can be further adapted to provide for measurement of forces on the micro-cantilevers of between 0.045 μN and 22.5 μN for each micro-cantilever. Where the spring constant of each micro-cantilever is 0.2 μN/μm, the device can be further adapted to provide for measurement of forces on the micro-cantilevers of between 0.02 μN and 10 μN for each micro-cantilever.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the disclosed subject matter. Together with the description, the drawings serve to explain the principles of the disclosed subject matter.

BRIEF DESCRIPTION OF THE DRAWINGS

FIGS. 14a and 14b illustrate effects of introducing compounds known to impact blood pressure to microtissue formed from smooth muscle cells in accordance with the disclosed subject matter.

FIG. 14b illustrates effects of introducing compounds known to impact blood pressure to microtissue formed from smooth muscle cells in accordance with the disclosed subject matter.

Figure 1A:
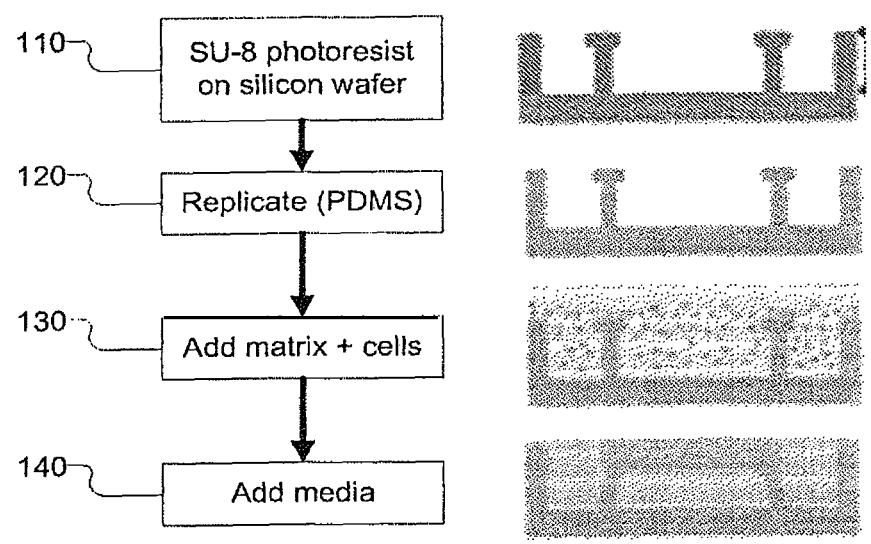
FIG. 1a is a simplified flow diagram of a method for generating microtissues in accordance with an embodiment of the disclosed subject matter.

Throughout the drawings, the same reference numerals and characters, unless otherwise stated, are used to denote like features, elements, components or portions of the illustrated embodiments. Moreover, while the disclosed subject matter will now be described in detail with reference to the Figs., it is done so in connection with the illustrative embodiments.

DETAILED DESCRIPTION

The disclosed subject matter provides systems and methods for the generation of microtissues. For purpose of illustration and not limitation, description of exemplary embodiments in connection with the generation of cardiac microtissues ("CMTs"), three-dimensional micro-scale constructs of cardiac cells embedded within collagen/fibrin 3d matrices, in micro-fabricated tissues gauges (μTUGs), will be made. The techniques disclosed herein can be used for the purpose of high throughput monitoring of the maturation, structure and function of cardiac tissues, and how these processes are impacted by physical factors, potential pharmacologic compounds, culture conditions, and targeted molecular-genetic manipulations. However, one of ordinary skill in the art will appreciate that tissues of any adherent cells can be used in connection with the disclosed subject matter, and the disclosed subject matter is not limited to cardiac microtissues.

In one aspect of the disclosed subject matter, devices for generation of microtissues are provided. For purposes of illustration, and not limitation, exemplary embodiments of devices for generation of cardiac microtissues will now be described with reference to FIG. 1, FIG. 2, and FIG. 3.

Figure 2:
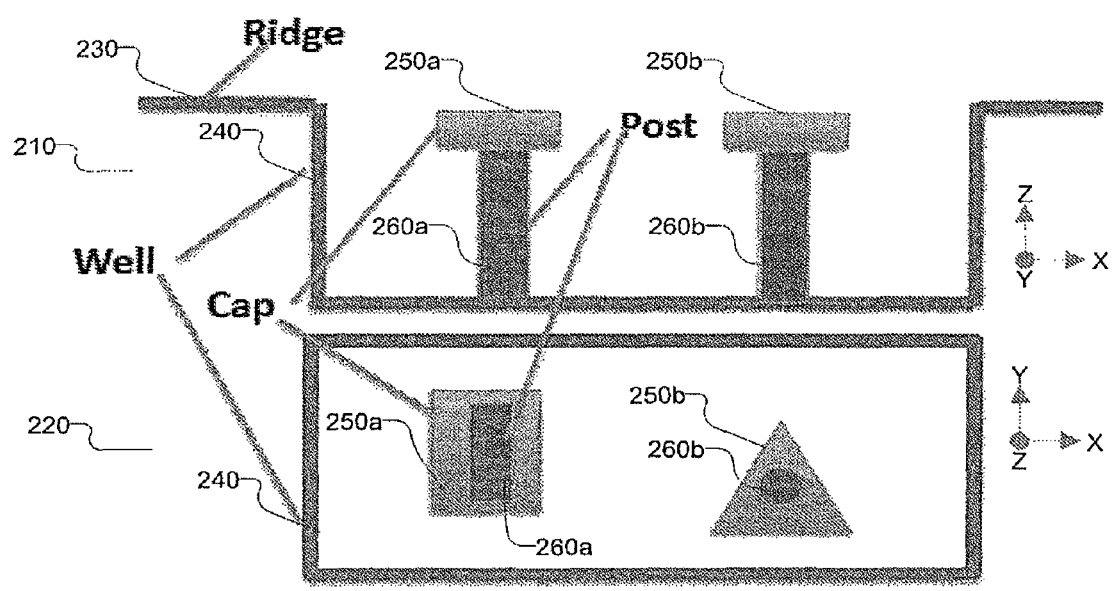
FIG. 2 is a diagram of a device for generating microtissues in accordance with an embodiment of the disclosed subject matter.

In one exemplary embodiment, with reference to FIG. 2, a micro-fabricated platform for the generation of microtissues can include one or more micro-wells containing a plurality of micro-cantilevers, each including a "post" (or "pillar," "micropillar") 260a and 260b (collectively 260) within each micro-well 240. FIG. 2 depicts a side view 210 and a top view 220 of an exemplary micro-well, or "micro-fabricated tissue gauge" (referred to herein as a "μTUG"). As used herein, the terms "micro-well," "micro-fabricated tissue gauge" and "μTUG" can be used synonymously. For purposes of illustration and not limitation, description of the exemplary embodiment depicted in FIG. 2 will be made with reference to orthogonal X, Y, and Z spatial dimensions, as shown in the figure.

The number of cantilevers in each micro-well can be, for example, two. Alternatively, a plurality of cantilevers can be located at predetermined locations within a micro-well. For example, the cantilevers can be arranged in a ring configuration, in a line configuration, in a square configuration, or any other configuration. The cantilevers can have a variety of suitable geometries. For example, the post 260a can have a rectangular geometry. Alternatively, the post 260b can have a cylindrical geometry. In certain embodiments, the posts 260 can have a height ranging from approximately 5 μm to approximately 1000 μm or larger. The thickness of each post 260 can also vary. In certain embodiments, the thickness of the posts 260 can be non-uniform. For example, the posts 260 can taper from the base to the tip, and/or can have vertical notches. One of ordinary skill in the art will appreciate that dimensions and geometries of the cantilever posts 260 can affect the stiffness of the cantilever posts 260 to bending, torsion, and movements of a desired application, discussed in more detail below.

In certain embodiments, the posts 260 can have an X and Y dimension substantially less than that of the Z dimension. For example, the width and depth of the posts 260 can be at least half of the height. Narrow posts can facilitate the formation of elongated tissues, without bulk tissue formation around the posts. Such elongated tissues can reduce stress at the connection with the post, and can provide greater stability in tissue formation and function.

Each cantilever can include a "cap" 250a and 250b (collectively 250) coupled to a terminal end of the post 260. The terminal caps 250 can also have a variety of suitable geometries, including, for example including but not limited to, a rectangular shape 250a or a triangular shape 250b. The caps 250 can have dimensions in the X and Y axis greater than the X and Y dimensions of the post 260, thus creating an "overhang." The caps can have X-Y dimensions ranging from, for example, approximately 5 μm to approximately 1000 μm. When tissues are generated in the micro-wells 240, as described in more detail below, the caps 250 can prevent the tissues from becoming dislodged from the posts 260. That is, for example, when a cardiac microtissue matures, it can be anchored by the posts 260 and can start beating or otherwise contract and exert a force on the posts 260, thus causing the posts 260 to bend. The caps 250 can further anchor the microtissue. In certain embodiments, each cantilever (i.e., post 260 and cap 250) can be configured in a "T-shape," such that the post is a narrow pillar and the cap forms the top of the T. Alternatively, each cantilever can have an "I-shape," such that the cantilever also has an extended base portion connected to the bottom of the micro-well 240. Moreover, the dimensions of the caps 250 can impact the stability of the device. For example, as disclosed herein in connection with certain embodiments, caps with oval shapes can experience a lower faction of breaking from the posts during the fabrication process.

In certain embodiments, the caps 250 can be used to measure force exerted on the posts 260 by a contracting tissue, as described in more detail below. In these embodiments, for example, the caps 250 can be formed from a fluorescent material. Alternatively, the caps 250 can be coated with a fluorescent material, e.g., with approximately 1-100 fluorescent beads per cap. In this manner, the caps 250 can be imaged using fluorescent microscopy. Alternatively, the caps 250 can include a textured surface with, e.g., topographic features such as angled groves, mesa's, pyramids, pits, or the like, for use in optical microscopy.

The cantilevers can be separated by a micrometer or millimeter scale distance within the micro-well 240. In certain embodiments, the separation distance between the cantilevers can be, for example, distances of 200 μm, 100 μm, 500 μm, 800 μm, 1 mm, or 5 mm. The micro-well 240 can be of any geometry. For example, in one embodiment, the micro-well 240 can be rectangular, optionally with rounded corners. One of ordinary skill in the art will appreciate, in light of the description below, that the geometry of the micro-well 240 can also impact the geometry and compacting of cells and microtissues therein. The micro-well 240 can be bounded by ridges 230. The ridges 230 can be flat or angled. In an exemplary embodiment, the ridges 230 can be adapted to de-wet (i.e., be absent of collagen) during the generation of microtissues within the micro-well 240, in particular prior to collagen polymerization. In this manner, each micro-well 240 can contain a separate body of fluid. As such, the dimensions of the ridges 230 can be designed such that de-wetting is enhanced.

In some embodiments, the micro-cantilevers (including the posts 260 and caps 250), along with the μTUG substrates (e.g., the micro-wells 240 and ridges 230), can be made of PDMS, while in others they can be made other rubber-like materials with elastic properties. Other silicone-based polymers such as rubber, polycaprolactones, or polyurethanes can also be used. Additionally, hydrogels including those made with polyacrylamide, polyethylene glycol can also be used. As disclosed herein, any material with elastic properties that does not exhibit creep can be used, including materials with viscoelastic properties.

In certain embodiments, the micro-cantilevers can have, for example, a stiffness range of 1-10 MPa, 10 kPa-1 MPa, 10 MPa-1 GPa, or 1-100 GPa. Each micro-cantilever can have a determinable spring constant, either known or obtained by calibration. For example, each micro-cantilever's spring constant can be calculated utilizing a capacitive MEMS force sensor mounted on a micromanipulator according to conventional methods, and/or can be estimated computationally based on geometric dimensions of the cantilevers along with known values for the Young's modulus of the material of the micro-cantilevers (e.g., PDMS).

Figure 3:
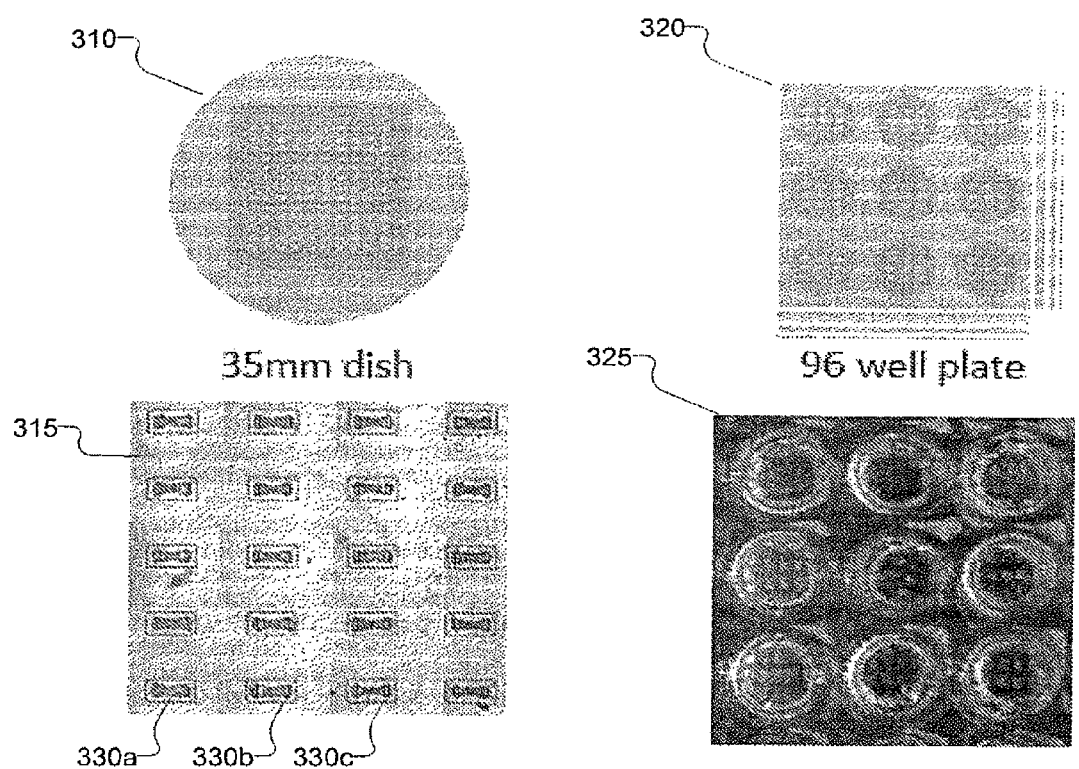
FIG. 3 illustrates platforms for generating microtissues in accordance with embodiments of the disclosed subject matter.

In an exemplary embodiment, with reference to FIG. 3, the micro-fabricated platform for the generation of microtissues can include an array of μTUG (e.g., an array of micro-wells 240, each including one or more micro-cantilevers including a post 260 and cap 250), separated by ridges 230. In one embodiment, for example, a 35 nm dish 310 can include a substrate including a plurality of patterned μTUGs. An image 315 of a portion of the μTUGs (including, e.g., a first μTUG 330a, a second μTUG 330b, a third μTUG 330c, and others (not labeled)) within the 35 nm dish is provided in FIG. 3. Alternatively, a 96 well plate 320 can include the μTUGs within the wells. Additionally or alternatively, 6, 12, 24, 48, 96, and 384 well plates can be used. The μTUGs can be grouped, for example, into nine discrete areas, each including nine μTUGs. For example, each discrete area can be a "well." That is, with the well plate 320 substrate, a plurality of "wells" can be formed, each well containing one or more micro-wells. As used herein, the term "well" can refer to a well in which one or more micro-wells is defined therein. Likewise, the term "96-well well" can refer to a well of the 96-well plate. An image 325 of the 96 well plate 320 in accordance with one embodiment is provided in FIG. 3.

In one embodiment, a "large format well" (e.g., μTUG substrate) can include an array of 10×13 μTUG micro-wells defined on the substrate, all spaced 800 microns apart, in a single well comprising the entire substrate. The array can cover a surface area of 1.9 cm×1.9 cm. The large format well can also include a plurality of grooves formed in the substrate adjacent to each micro-well for insertion of electrodes, as described below.

In an exemplary embodiment, a well plate (e.g., 96-well plate) can have a plurality of wells. There can be up to 9 micro-wells in each well, and in an exemplary embodiment there can be 1-3 μTUG micro-wells per 96-well well. That is, for example, each well-plate can include 96 wells, and each well can include 1-3 micro-wells (e.g., micro-well 240 in FIG. 2). The spacing between adjacent sets of μTUG wells (e.g., the 96 wells) can be 9 mm to align with the spacing between adjacent wells in a standard 96-well plate. The 1-3 μTUGs micro-wells within each 96-well well can be spaced 150 microns apart, although in certain embodiments spacing of 100, 200, 300, 400, 600 and 800 can be used. Such spacing can enable the isolation of a suspension of collagen and cells in adjacent μTUG micro-wells. The 1-3 μTUG micro-wells can be parallel in their orientation. The diameter of the bottom surface of each 96-well well can be, for example, 2.5 mm. Additionally, rather than aligned with the center of the 96-well well, the μTUGs can be shifted to laterally (e.g., in the X or Y dimension) by approximately 200-250 microns, with the middle μTUG micro-well shifted by an additional 200 microns. Such an arrangement can create additional space for an aspiration tip to access the device surface during de-wetting. In an exemplary and non-limiting embodiment, 3 μTUGs can fit within a 2.5 mm diameter circular surface area, but the surface area can have other diameters, such as a diameter of 1, 1.5, 2, 2.5, 3, 4, 5 or 6 cm, as well. With larger diameter surface areas, more μTUG micro-wells can be incorporated into an SU8 master.

In an exemplary embodiment, each micro-well contains two posts (micropillars). Each micro-well can have dimensions of 800 μm wide by 800 μm deep, by 400 μm tall. Each micropillar can 45 μm thick (e.g, in the dimension of the micropillar that is parallel with the longitudinal dimension of the micro-well), 100 μm wide (e.g., in a dimension perpendicular to the longitudinal dimension of the micro-well) and 140 μm tall. The micropillar can have a rounded rectangular cross-section. The cap part of each micropillar can 85 μm thick, 140 μm wide and 40 μm tall. The cap can have a rounded rectangular cross-section. Therefore, the total height of the micropillar and cap combined can be 180 μm tall. The two pillars can be arranged at opposite ends along the longitudinal dimension (e.g., 800 μm) of the micro-well.

Alternatively, the devices can have "wider" pillars in which the micropillar is 45 μm thick, 160 μm wide and 140 μm tall. In this embodiment, the caps can be 85 μm thick, 200 μm wide and 40 μm tall. Alternatively, the caps can have a more elliptical cross-section which can facilitate easier casting of the device (e.g., less ripping of caps off the micropillar). In an exemplary embodiment, the micropillar spacing is 480 um, center-to-center between two pillars, however this dimension and others can be varied. For example, the micropillar thickness can be 30 to 85 μm for heights of 140 um. The micropillar height can be fabricated up to 2 mm tall. For these tall micropillars, the micropillar thickness can be up to 1.2 mm (or thicker). Concomitantly, the cap dimensions can always be slightly larger than the micropillar dimensions. Micropillar spacing can also be varied, depending on how large the micro-well is. For example, micropillar spacing can be up to 7 mm for large micropillar and micro-well configurations.

In certain embodiment, the micro-fabricated platform, e.g., a large format well or wells of a well plate, including the plurality of micro-wells, can include an upper portion having a conical shape. For example, the upper portion can have a wall suitable to retain a suspension of cells, and the wall can have an angled contour such that when centrifuged, the cells in the suspension can be driven into the micro-wells along the angled contour. In certain embodiments, the upper portion can be formed from a separate layer of material, and can be coupled to the lower portion of the platform including the wells with conventional techniques, such as UV bonding, heating, or the like. In this manner, the techniques disclosed herein can reduce the total number of cells required to sustain tissue formation, which can reduce cost for the creation of high throughput screening applications.

In certain embodiments, for example in connection with a 96-well plate, each micro-well well can be cast on a single slab of PDMS with a single negative old. A separate well gasket layer can be bonded to the resulting substrate, such that the gasket layer has defined therein the 96-well wells, and is bonded such that the 96-well wells are aligned to group the micro-wells formed in the substrate within each 96-well well. Alternatively, the 96-well wells can be cast from a 96-well plate negative mold, and each micro-well negative mold can be added for each 96-well well. In this manner, the micro-wells can have different orientations in different wells.

For purposes illustration and not limitation, in certain embodiments, a 96-well well plate can include a 96-well PDMS gasket and PDMS μTUG substrate that can be reversibly sealed. The 96-well PDMS μTUG substrate can be cast on a thin slab of PDMS, and the PDMS wall can be optionally trimmed away. The 96-well PDMS gasket can be fabricated by generating a negative mold of a flat-bottom 96-well plate. The flat-bottom negative mold can be silanized and used to cast a positive gasket with a flat-bottom (e.g., approximately 6.4 mm in diameter). Alternatively, the 96-well PDMS gasket can consist of consist of round-bottoms, and cast in a similar fashion. Alternatively, in an exemplary embodiment, a conical-shaped 96-well can be punched out with a 2.5 mm biopsy punch. For example, 1, 1.5, 2, 2.5, 3, 4, 5 and 6 mm biopsy punches can be used to punch holes of different sizes. After the holes are punched, the 96-well PDMS gasket can be aligned and overlaid on the 96-well PDMS substrate. As disclosed herein, a conical-shaped profile can have the advantages that cells can be strongly concentrated in the punched holes when driven down via centrifuging, and that fabrication can be facilitated with punching in a conical-shape well rather than flat or round bottom wells.

In like manner, in certain embodiments, the micro-wells 240 within the platform can be arranged proximal to each other, separated by the ridges at a small distance. Reducing the spacing between the micro-wells can reduce the total number of cells required to sustain tissue formation. However, the distance between each micro-well can affect the feasibility of de-wetting the platform, and thus can be sufficiently large depending on the viscosity of the suspension of cells. For example, in certain embodiments, the distance between the micro-wells can be approximately 100 microns.

In one exemplary embodiment, with reference to FIG. 1, for purpose of illustration and not limitation, the micro-fabricated tissue gauges can be fabricated according to the following exemplary process: Layers of Su-8 photoresist (e.g., available from Microchem) can be patterned onto a silicon wafer (110) by successive spin coat, alignment, exposure and bake processes. An exemplary process for producing wider caps 250 that overhang on the tips of the cantilever posts 260, in order to anchor the contracting gel, can include spin-coating and soft-baking the second layer of UV blocking solution (30% S1813, 70% Su-8 2010). This solution can be strong enough to block 85% of UV but still contain enough Su-8 to facilitate complete cross linking between the top (caps) and bottom sections (posts). Although a range of geometries of the cantilevers and micro-wells can be adjusted to accommodate different applications using this same process, other fabrication processes such as reactive ion etching and positive resists can also be employed to generate the desired geometries. PDMS (e.g., available from Sylgard 184, Dow-Corning) µTUG substrates can then be molded (120) from Su-8 masters with an additional step of embedding fluorescent microbeads (e.g., available from Fluoresbrite 17147, Polysciences Inc.) into the cantilevers to accommodate computerized cantilever deflection tracking. PDMS stamps can then be submerged in ethanol and treated in an ultrasonic pen cleaner (e.g., available from Model 600, Rotex Co.) to displace air trapped in the inverted pattern. After a period of time (e.g., 5 minutes), the stamps can be transferred into the wells of a multi-well plate (e.g., 6 to 96-well plate, as illustrated in FIG. 3). For a 6-well plate, although not required, a 10 ml of ethanol and fluorescent bead solution (e.g., 3000:1) can be added to each well. The six-well plates containing stamps can then be centrifuged for 1 minute at 1000 rpm to settle the fluorescent beads into the pattern on the stamps. The ethanol can then be allowed to evaporate overnight at room temperature, leaving the beads behind covering the entire patterned surface. PDMS molds can then be cast onto the stamps to produce the final µTUG substrates. As a result, the fluorescent beads covering the stamp can be embedded in the surface of the substrates.

In one embodiment, the base layer can be fabricated with SU8-2002. The soft baking times for the post and cap layers can be 3.5 hours 2.75 hours, respectively, for fabrication of the master. The blocking layer photoresist formula can be, for example, 30/70% S1813/SU8-2010. Such techniques can provide for improved durability and improved adhesion of the SU8 caps to the posts. Alternatively, the base layer can be fabricated with SU8-2050, and the soft baking times for the post and cap layer can be 30 minutes each, and the blocking layer photoresist formula can be 15/85% S1813/SU8-2007.

Figure 15:
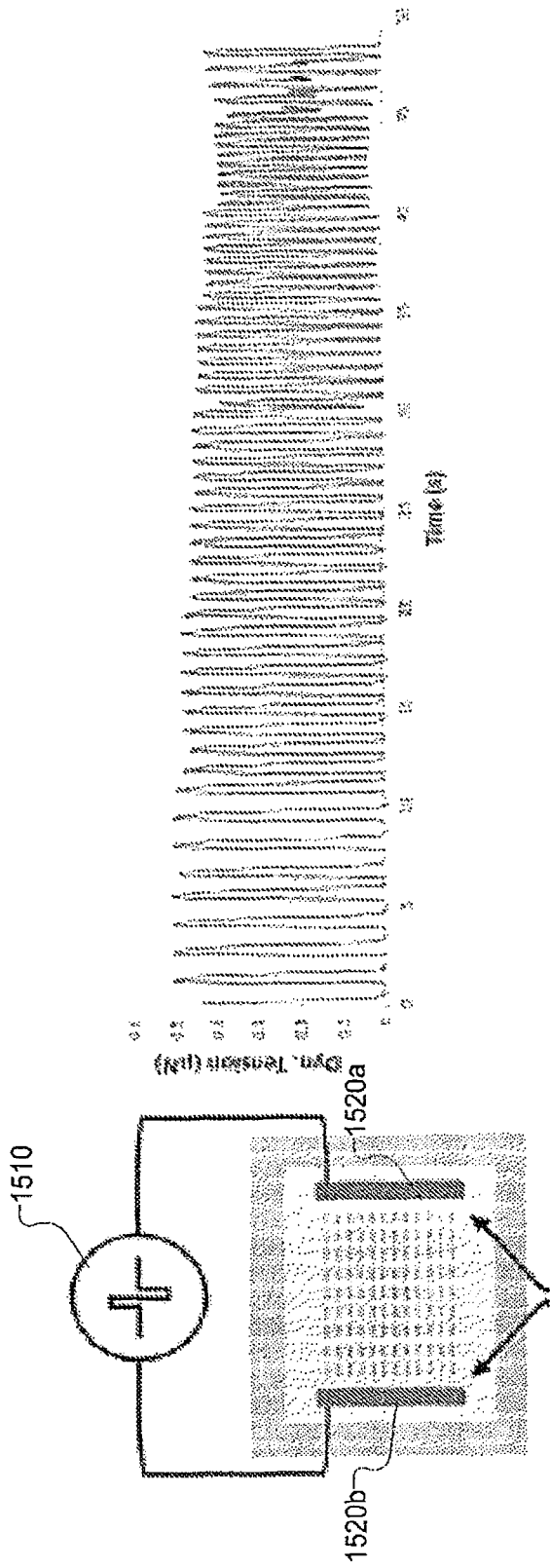
FIG. 15 is a diagram of a device for electrically stimulating the microtissues in accordance with one embodiment of the disclosed subject matter.

In certain embodiments, and with reference to FIG. 15, electrodes 1520a and 1520b (collectively 1520) can be arranged proximal to the micro-wells 240. For example, two parallel carbon electrodes can be inserted on both sides of the array of micro-wells to simultaneously stimulate the arrays of CMTs. One of ordinary skill in the art will appreciate that the electrodes 1520 can be arranged in a variety of other configurations and can be formed from a variety of suitable materials. The electrodes 1520 can be electrically coupled to a voltage control circuit 1510, e.g., with platinum wires. The voltage control circuit 1510 can be adapted to provide an oscillating voltage to the electrodes at a particular frequency. In some embodiments, the voltage control circuit 1510 can be tunable such that the frequency of oscillation can be adjusted. The oscillation of applied voltage can be, e.g., sinusoidal, square wave, sawtooth, or the like. In an exemplary embodiment, the voltage control circuit 1510 can be configured to oscillate at a frequency in the range of approximately 0.2 Hz to 1 Hz, with 1 ms square biphasic pulses at 6V/cm. Electrical stimulation can be initiated after a period of time after the cell suspension is driven into the micro-wells, which can affect cell alignment and force generation within the CMTs, as described in more detail below. In other embodiments, the microtissues can be field-stimulated at 1, 2, or 3 Hz.

To generate the microtissues within the µTUGs, cells can be delivered into the micro-wells 240 with a matrix pre-polymer. For example, the micro-fabricated platform can be immersed in a suspension of cells and a reconstitution mixture including collagen and fibrinogen. The suspension of cells and reconstitution mixture can be driven into the micro-wells (130), and the collagen polymerized to form a matrix. In certain embodiments, the solution can be driven into the micro-wells using a centrifuge in connection with a spin and de-wetting technique. Alternatively, a direct micro-injection or bio-printing technique can be used to introduce the solution into the micro-wells. As used herein, the term "driving" in connection with the insertion of a solution of cells into the micro-wells can include using a centrifuging technique, bio-printing technique, direct micro-injection technique, or the like. The cells can then be cultivated over time (e.g., with the introduction of media (140), so as to form cell-cell contacts and spontaneously compact the matrix, such that the micro-cantilevers anchor the matrix and constrain the contraction of the matrix to form a linear band of cardiomyocyte-containing microtissues that spans across the top of the micro-cantilevers.

As disclosed herein, the cells can be driven towards a top surface of the suspension after de-wetting but prior to polymerization of the extracellular matrix. For example, in certain embodiments, the cells can first be driven into a plurality of micro-wells (e.g., micro-wells 240 as illustrated in FIG. 2) on a well plate (e.g., as depicted in FIG. 3). After de-wetting to isolate a population of cells into each micro-well (i.e., such that the surface of the solution in each micro-well is bounded by ridges—e.g., ridge 230 as illustrated in FIG. 2), the well plate can be inverted and centrifuged so as to drive the cells within the solution toward the top surface of the solution. In this manner, a linear band of tissue can form at the top of the micro-well, constrained by a top portion of each post and anchored by each cap so as to prevent slipping.

For purposes of illustration and not limitation, an exemplary technique for adding cells in accordance with an exemplary embodiment will now be described. Centrifugation can be employed in steps in connection with a 96-well plate µTUG substrate. For example, Pluronics can first be dispensed over the µTUG substrate and spun into the µTUG micro-wells to dislodge air bubbles. Alternatively, in connection with different cell types, different concentrations of Pluronics, e.g., F127, can be spun into the wells at between approximately 3 and 30 minutes. Such techniques can decrease the time for seeding and collagen de-wetting. Collagen solution (e.g., Collagen and Fibrinogen) can be dispensed in 96-well well-plates, on ice, to pre-wet the µTUG micro-wells. The substrates, on ice, can then be de-gassed under vacuum to remove bubbles trapped in the μTUG micro-wells, and spinning at 3000 RPM for 3 minutes (rotating the substrate holder 90 to 180 degrees after 1.5 minutes) to dislodge any remaining bubbles. Such techniques can provide improvements relative to pipetting each well individually to remove bubbles, as the collagen/fibrinogen can start to polymerize and become difficult to de-wet with increased processing time. Furthermore, pipetting each well individually can produce-non-uniform results as small bubbles can be trapped in certain wells, but not others, which can increase seeding heterogeneity.

After pre-wetting, a suspension of collagen, fibrinogen, and cells can be added. The cells can then be spun into the wells, e.g., at 1200 RPM for 3 minutes. The substrate can be rotated 180 degrees during spitting (e.g., after 1.5 minutes). This can uniformly distribute the cells within the μTUG micro-wells, which can provide for enhanced tissue fabrication, for example in connection with cardiac microtissue fabrication.

After spinning the cells into the μTUG micro-wells, the excess collagen/fibrinogen/cell solution can be de-wetted. De-wetting can be accomplished by, e.g., aspiration. For example, a 10 μL micropipette can be attached to an aspirator to access an area adjacent to the μTUG micro-wells. After de-wetting, the μTUG substrate can be inverted and spun to drive the cells toward a top surface of the μTUG micro-well, which can enhance the yield of tissues formed around the caps of the micro-cantilevers. Without such a technique, tissues can form around the base or mid-section of the micro-cantilevers, thereby making force more difficult to accurately measure. Moreover, tissues that are not formed at the cap level (e.g., at the top of the posts) can slide down the cantilevers, and as such centrifuging to drive the cells toward a top surface of the micro-wells can reduce such sliding. Spinning can include, based on the type of cells seeded, spinning at between approximately 500 RPM and approximately 1000 RPM. After de-wetting, the cells can be cultivated. In certain embodiments, cultivation can include humidification to prevent the μTUG tissues from drying out and prevent warping of the collagen gel to enhance cell distribution. Likewise, after polymerization of the collagen, media can be added individually to each well, and spun into each μTUG to remove air bubbles, to prevent the drying-out of the tissues.

In certain embodiments, the matrix prepolymer can alternatively include any type of isoform of natural extracellular matrix protein alone or in combination, including but not limited to collagens, elastins, fibrin, fibronectins, laminins, vitronectin, hyaluronic acid, and glycosaminoglycans. Furthermore, the matrix prepolymer can also include synthetic or partially synthetic materials or their derivatives such as, for example, polyacrylamide, polyethylene glycol, hyaluronic acid, albumin, DNA, RNA, peptides, self-assembling peptides, actin, and/or nanofibers.

For purpose of illustration and not limitation, introduction of neonatal rat myocytes into the micro-wells will now be described in connection with one embodiment of the disclosed subject matter. In this embodiment, the suspension of cells and reconstitution mixture can contain cardiomyocytes isolated from, e.g., 0-1 day old neonatal Sprague Dawley rat pups according to conventional methods. The reconstitution mixture can include 1 mg/mL or 2.5 mg/mL liquid neutralized collagen I from rat tail and 0.5 mg/mL fibrinogen from bovine plasma. The suspension of cells and reconstitution mixture can be applied to the platform and then driven into the micro-wells by centrifuging. Excess collagen, fibrinogen and cells can be removed by de-wetting the surface of the platform. The collagen can be polymerized so as to form a matrix by incubating the platform at a suitable temperature, which in one embodiment can be 37° C.

In some embodiments, the suspensions of cells and reconstitution mixture can contain human cardiac microtissues (hCMTs). For example, the CMTs can be developed with primary human cells that can be reprogrammed to a cardiac phenotype. Additionally, the CMTs can be developed by seeding with cardiac myocytes derived from human induced pluripotent stem cells (iPSCs). Live cells can be sorted based on SIRPA, a myocyte-specific surface marker. Epicardial fat fibroblasts and ventricular myocytes can be used as starting material for producing iPSCs and cardiac myocytes. Because adult cardiomyocytes do not expand in culture and isolation of such cells from living patients can involve appreciable risk, induced pluripotency of adult primary human cells can provide a viable expandable source of cells that can provide an unlimited supply of human cardiac myocytes for in vitro studies. Relatively low rates of cardiac cell differentiation and selection from embryoid bodies can be improved with alternative approaches that can combine bone morphogenic proteins with other agents. Such techniques can also provide efficient production of patient-specific CMTs.

The techniques disclosed herein can be used with myocardial cells, including cardiac myocytes and fibroblasts, of human origin. The CMT arrays can represent a range of patient-specific CMTs, with a realistic representation of human genetic diversity, and can be used for drug screening. The hCMTs can include different sources of iPSCs, variable purity of the myocytes included in CMTs, and fundamental differences in the phenotypes of the iPSC-derived myocytes (e.g., atrial, ventricular, pacemaker). One shortcoming of conventional delivery of medical therapies is that it is often applied uniformly and blindly across a broad population of people, even when it is known that for most such interventions only a percentage of those people will respond favorably and even another percentage might respond adversely to the same treatment. The source of this variability is often unknown but is thought to be specific to each person's biological state, be it their genomic, environmental, exposure history, or other background. As such, one use for microtissues is to generate them from cells sourced from specific individuals or populations with notable characteristics, be they adult, iPS-derived, or other type of cell, and study how that specific person or population responds to a particular therapeutic. Accordingly, the techniques disclosed herein can customize decisions on treatment options for individual patients or populations, or help with selection of patients during clinical trials.

To limit heterogeneity related to variable purity, prior to seeding the CMT arrays, FACS sorting based on positive selection for SIRPA can be employed, which can produce greater than 98 troponin T positive cells from human iPSCs. To minimize heterogeneity arising from different proportions of atrial, ventricular and pacemaker myocytes in CTMs, a differentiation protocol such as BMP2-induced SSEA-1$^+$ cells, associated with high rates of ventricular myocyte differentiation, can be employed. Additionally, immunohistochemical staining of the ventricle-specific gene TBX5 can be performed on a sample of CMTs to track proportion of ventricular versus other myocyte cell types. Additionally, CMTs from patients with muscular dystrophy-associated cardiomyopathy, or any disease-causing mutation, can be studied with the CMT platform disclosed herein to establish an in vitro model of human disease.

For example, hCMTs can be formed on the platform including a plurality of micro-cantilevers. The hCMTs can be generated from readily available cells. In some embodiments, the hCMTs can include hCMTs from at least one specific human genetic background. Alternatively, the hCMTs could, for example, include hCMTs from a plurality of different specific human genetic backgrounds. The hCMTs from various backgrounds can be observed within the microfabricated platform including a plurality of micro-cantilevers to determine whether specific human genetic backgrounds give rise to different responses to various perturbations. For example, in one embodiment, hCMTs can be derived from individuals with disease-causing mutations, such as patients with Duchenne muscular dystrophy, to create in vitro models of human disease.

In some embodiments, the suspensions of cells and reconstitution mixture can contain non-cardiac cells. For example, the mixture can contain smooth muscle, skeletal muscle cells, fibroblasts, myofibroblasts, or a combination thereof. The use of non-cardiac cells with the devices disclosed herein can allow for characterization of the contractility of these tissues and used to identify novel targets, molecules, proteins, and drugs to modulate muscle contractility. Moreover, in certain embodiments, the cells can include diseased cells, normal cells, or a mixture thereof. Such cells can additionally or alternatively include, but limited to, cells of mesodermal, ectodermal, or endodermal lineage, embryonic or adult stem cells, fibroblasts, endothelial cells, smooth muscle cells of any origin, skeletal muscle cells, cardiac myocytes, myofibroblasts, epithelial cells, neuronal cells, glial cells, astrocytes, hepatocytes, kidney epithelial cells, intestinal cells, lymphocytes, leukocytes, cells of human origin, cells of non-human origin, mouse cells, rat cells, rabbit cells, pig cells, bovine cells, primate cells, non-mammalian cells, fish cells, insect cells, mold cells, dictostelium cells, worm cells, *drosophila* cells, cancer cells, cell lines, non-eukaryotic cells, bacteria, and/or viruses.

In certain embodiments, the seeding of the cells can vary depending on the size and dimensions of the micro-wells 240 and the type of cells introduced. One of ordinary skill in the art will appreciate that an appropriate cell density can be varied depending on the desired application and/or particular size and dimensions of the micro-wells. However, for purposes of illustration and not limitation, cell density for myocytes can range from, for example, 1,000 cells per mL to 100,000,000 cells per mL, and lead to seeding of 1 cell per device, 2 cells per device, 2-5 cells per device, 5-10 cells per device, 10-100 cells per device, 10-50 cells per device, 50-100 cells per device, 100-200 cells per device, 200-400 cells per device, 400-1000 cells per device, 1000-10,000 cells per device, 10,000-100,000 cells per device, or the like.

In certain embodiments, the concentration of the collagen in which cells are embedded can also be varied from 1.5 to 9 mg/mL (giving a range of ECM stiffness from 0.5 to 12 kPa, similar to the ranges observed during cardiac tissue development). Additionally, the stiffness of the PDMS pillars against which the microtissues contract can be varied. By altering the geometry of the pillars and stiffness of PDMS itself, pillar stiffness can be varied by thirty-fold, mirroring the effects of afterload on cardiac tissue development. For purposes of illustration and not limitation, the feedback of boundary rigidity versus matrix stiffness can effect CMT contractions. Whereas both stiff cantilevers and stiff matrix result in higher cell tension, the cell alignment stays limited by the mechanical resistance of the stiff matrix, leading to lower cross-sectional stress The cells can be cultivated over time by addition of the appropriate media (140) to each platform. Over cultivation time, the cells can spread inside the matrix, form cell-cell contracts, and spontaneously compact the matrix over several days. The micro-cantilevers can anchor the contracting matrix, constraining the contraction of the collagen/fibrin matrix to form a linear band of cardio microtissues that spans across the top of the micro-cantilevers.

As embodied herein, the cell suspension mixture driven into the micro-wells can initially contain evenly distributed amorphous round heart cells. Over time, the cells can elongate and align along the axis between the micro-cantilevers. As cultivation continues, the cells can being spontaneously beating as single cells. As cultivation further continues, the cells start to beat coherently, bending the micro-cantilevers toward each other at each contraction.

In one exemplary embodiment, enriched iPSC-derived human myocytes and human fibroblasts can be suspended (e.g., 1 million cells/mL) in an ice-cold neutralized solution of collagen (1 mg/mL), overlaid onto the microtissue arrays, centrifuged into the micro-wells, dewetted to leave the cell/collagen suspensions only in the micro-wells, warmed to 37° C. to allow collagen to gel, and then immersed in high glucose DMEM (Mediatech, Inc.) containing 10% horse serum (Invitrogen), 2% chick embryo extract (Charles River Laboratories International, Inc.), 4 mM L glutamine, 1 mM sodium pyruvate, 100 units/mL penicillin, and 100 mg/mL streptomycin (all from Invitrogen). Cells will then reorganize to form a microstrip around the two elastic pillars within each of the, for example 200 micro-wells per chip over the first 24 hours.

Figure 1B:
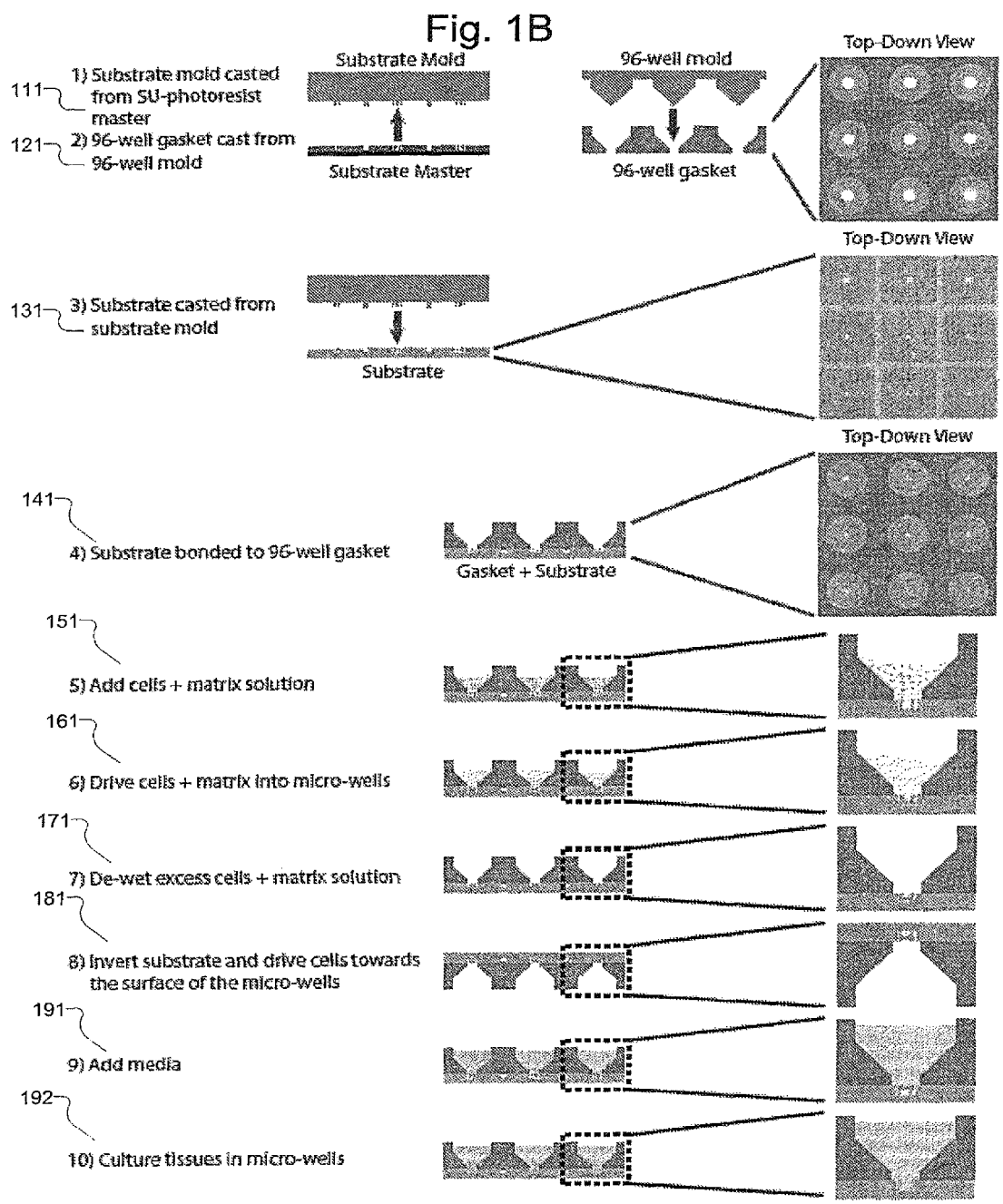
FIG. 1b is a flow diagram of an exemplary method for generating microtissues in accordance with an embodiment of the disclosed subject matter.

For purpose of illustration, and not limitation, description will now be made, with reference to FIG. 1b, of exemplary techniques for fabrication of a device for generating microtissues and for the generation of microtissues.

In this exemplary embodiment, for example, a substrate mold can be casted from a SU-photoresist master 111 to form a substrate mold. The substrate mold can be, for example, patterned the negative of a plurality of micro-wells. A 96-well gasket can be cast from a 96-well mold 121. A substrate can be casted from the substrate mold 131. The substrate can be formed, for example, with the micro-wells formed therein arranged in groups corresponding to each well of the well-gasket formed from the well-mold. As depicted in FIG. 1b, each well corresponds to a single micro-well, however in certain embodiments additional micro-wells can be arranged within each well (e.g., 3 micro-wells). The substrate can be bonded to the 96-well gasket 141, such that each well of the 96-well gasket is aligned with each group of micro-wells corresponding thereto.

A suspension of cells and matrix solution, e.g., prepolymer matrix, can be added to each well 151. The cells and matrix solution can be driven into each micro-well 161, e.g., via centrifuging. The excess cells and matrix solution can be de-wetted 171 such that each micro-well includes an isolated suspension of cells and matrix solution each with a top surface bounded by the ridges of each micro-well. The substrate can then be inverted and the cells can be driven toward the surface of the micro-wells 181, e.g., via centrifuging. Media can then be added 191 and the cells can be cultured 192 to form micro-tissues in the micro-wells. Additionally, for purposes of illustration and not limitation, each well can be raised on its own "island," thereby forming a gap between the gasket and the substrate in the space between each well. Such a configuration can reduce photoresist cracking in connection with the SU-8 master, and can enhance device yield from each master.

For purpose of illustration, and not limitation, description will now be made of techniques for generation of microtissues within the devices described above with reference to FIG. 4 and FIG. 5.

As noted above, the cells can be cultivated over time by addition of the appropriate media to each platform. Over cultivation time, the cells can spread inside the matrix, form cell-cell contracts, and spontaneously compact the matrix over several days. The micro-cantilevers anchor the contracting matrix, constraining the contraction of the collagen/fibrin matrix to form a linear band of cardio microtissues that spans across the top of the micro-cantilevers. While the cell suspension mixture driven into the micro-wells can initially contain evenly distributed amorphous round heart cells, over time, the cells can elongate and align along the axis between the micro-cantilevers. As cultivation continues, the cells can being spontaneously beating as single cells. As cultivation further continues, the cells start to beat coherently, bending the micro-cantilevers toward each other at each contraction.

In one embodiment, microscale constructs of cardiac cells within collagen/fibrin 3D matrices can be generated using microfabricated arrays of micro-wells within a PDMS mold as described above. For a period of time 435 after cell seeding, the collagen/fibrin matrix can contain evenly distributed amorphous round heart cells, as illustrated in image 510 of FIG. 5. Over time, cells can elongate, aligned along the axis between the cantilevers, and can start to beat as single cells. For example, image 520 illustrates the cells two days after seeding, image 530 illustrates the cells three days after seeding, and image 540 illustrates the cells seven days after seeding.

The time from seeding to tissue assembly can range from hours to days. Such a time period can depend on, among other things, the type of cells introduced, the geometry of the micro-wells and/or cantilevers, and the composition of the prepolymer matrix. For example, different cell types can remodel and contract extracellular matrix at different rates. Fibroblasts, for example, can contract collagen within 3-4 hours. uTUG tissues comprised of only fibroblasts can be fully contracted within 24 hours. Fibroblast seeding can be sparse (e.g., with 10-25% of the micro-well filled). Too many fibroblasts can lead to tissue detachment from the micropillars due to collagen rupture or slippage. Additionally, for example, tissues comprised of cardiomyocyte can take 2-3 days to fully contract around the posts of the micro-well and another 1-2 days to establish excitation-contraction coupling, and exhibit spontaneous or synchronous beating. A lower density prepolymer matrix can lead to faster tissue contraction and remodeling, while a higher density prepolymer matrix can take longer to contract. Culturing the microtissues in media with certain growth factors can also affect tissue assembly.

The time from seeding to tissue maturation can range from hours to weeks. Such a time period can likewise depend on, among other things, the type of cells introduced, the geometry of the micro-well and/or cantilevers, and the composition of the prepolymer matrix. For example, in order to mature, stable anchoring of the tissues on the micropillars of the micro-well can be required. Thus for microtissues comprised of highly contractile cells (e.g., fibroblasts), stiffer micropillars can be used. If the micropillars are too soft, the tissue can contract to such an extent that it can detach from one or more of the micropillars. Stresses on the micropillars can build up as the cells contract the matrix around the micropillars. These stresses can be localized at edges, corners and areas of roughness on the micropillar caps.

As such, the geometry of the microcantilever cap (rounded rectangles, oval shaped, circular shaped) can affect tissue stability and maturation. The width of the micropillar and cap can also have an effect. Wider micropillars can form "dog-bone" shaped tissues that are wide around the pillars and narrow in the middle. By contrast, narrow micropillars can tend to anchor tissues with a more uniform cross-section. These differing cross sectional profiles can have different micro-structures as a result of different cell alignment, cell distribution and matrix remodeling. In an exemplary embodiment, using narrow pillars with rounded caps can yield longer-lasting cardiac microtissues.

Figure 4:
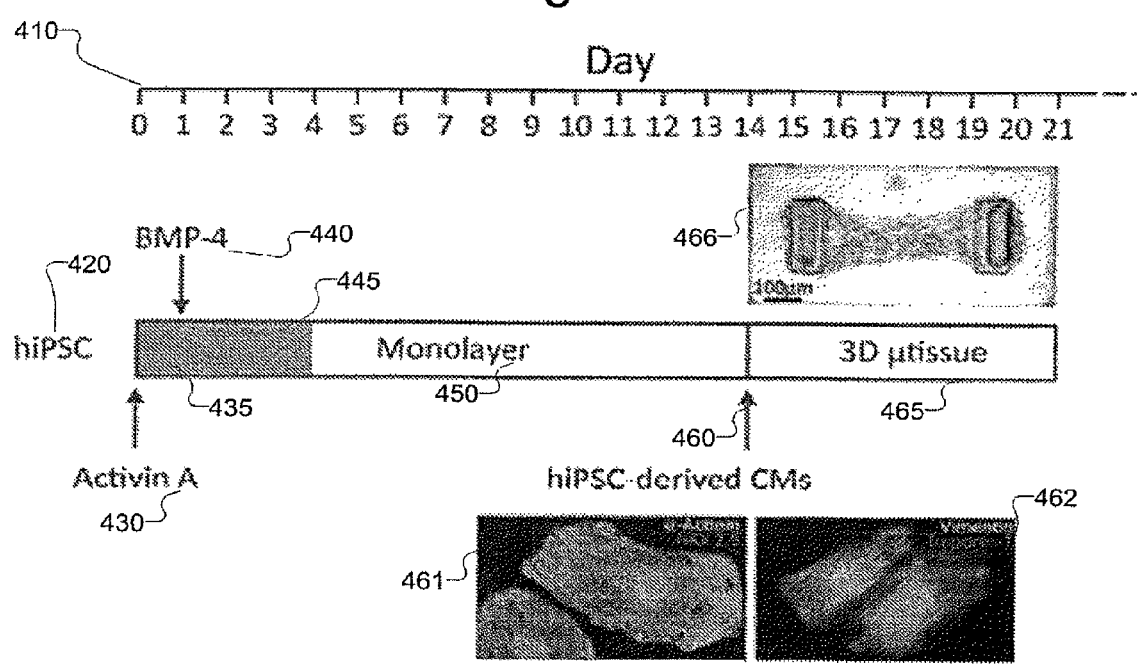
FIG. 4 illustrates the timeline of the generation of microtissues in accordance with an exemplary embodiment of the disclosed subject matter.

In an exemplary embodiment, with reference to FIG. 4 one illustrative and exemplary embodiment can provide for the study of cardiomyocytes derived from iPSC cells. As illustrated in FIG. 4, human iPSC cells 420 can be seeded into the μTUGs. FIG. 4 depicts a timeline 410 for the differentiation of iPS cells into a cardiac precursor, which can change and improve as the field progresses. As illustrated in FIG. 4, such cells can be seeded into the devices at an arbitrary point during the differentiation process, and the cells can be tested at a later point in time. In an exemplary embodiment, activin A 430 can be introduced upon the seeding of hiPSC cells. After a day, BMP-4 440 can be introduced. After four days, a monolayer 450 of cells can form, and after fourteen days, a 3D microtissue 466 can form. As disclosed herein, for example, hiPSC derived cardiomyocytes, illustrated in images 461 and 462 prior to seeding, can be introduced, e.g., at day 14 460.

Figure 6:
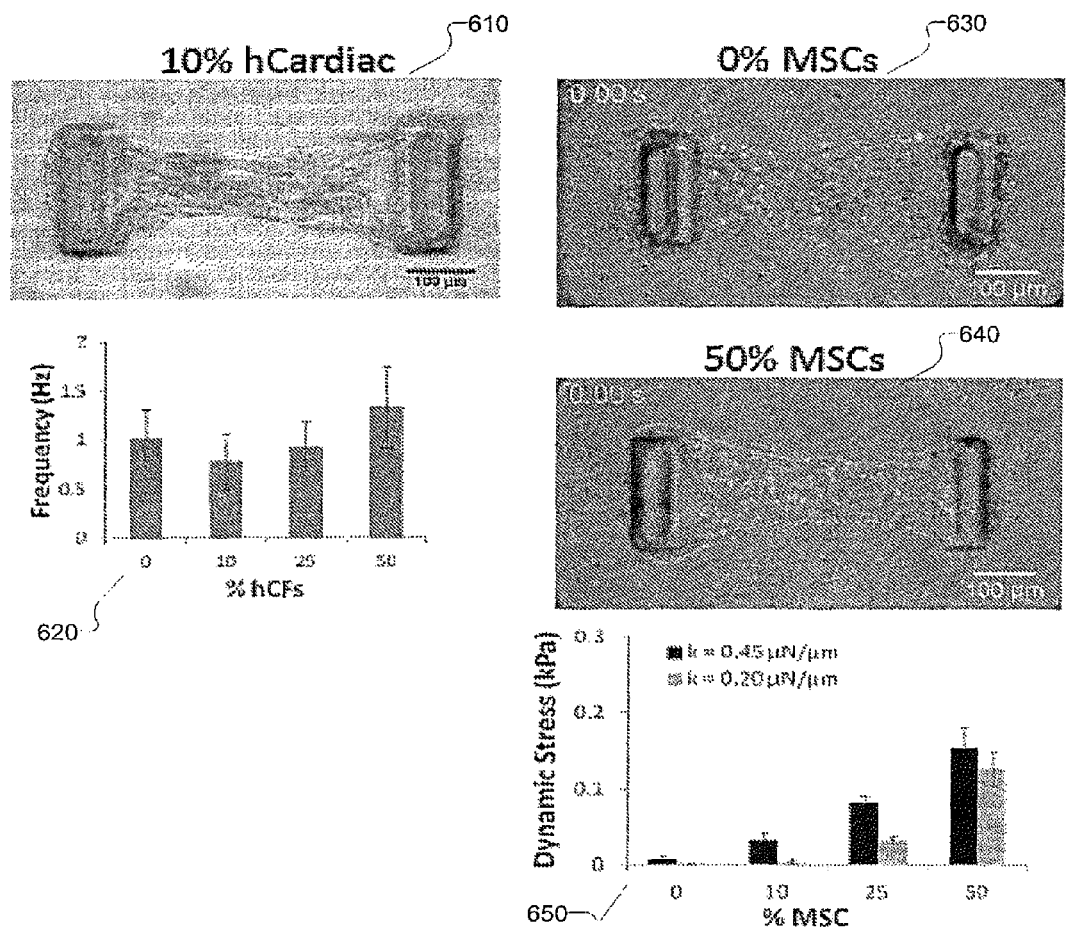
FIG. 6 illustrates the impact of introducing different cell types into the devices in accordance with the disclosed subject matter.

For purposes of illustration and not limitation, and with reference to FIG. 6, mixtures of cardiomyocytes with other cell types can be introduced into the micro-wells. For example, mixtures of cardiomyocytes with other cell types. For example, image 610 illustrates a microtissue formed by mixing cardiomyocytes with human cardiac fibroblasts. Additionally, cardiomyocytes can be mixed with human mesenchymal stem cells, as illustrated in image 640. For purpose of illustration, image 630 depicts a microtissue formed without introduction of human mesenchymal stem cells. As is evident from the images and corresponding graphs, introduction of such cells can impact tissue organization and function. For example, as illustrated in graph 620, beat frequency of the resulting microtissue formed from cardiomyocytes and human cardiac fibroblasts can vary with the concentration of human cardiac fibroblasts introduced. Likewise, as illustrated in graph 650, dynamic stress in the resulting microtissue formed from a mixture of cardiomyocytes with human mesenchymal stem cells can vary according to the concentration of human mesenchymal stem cells introduced.

Figure 14B:
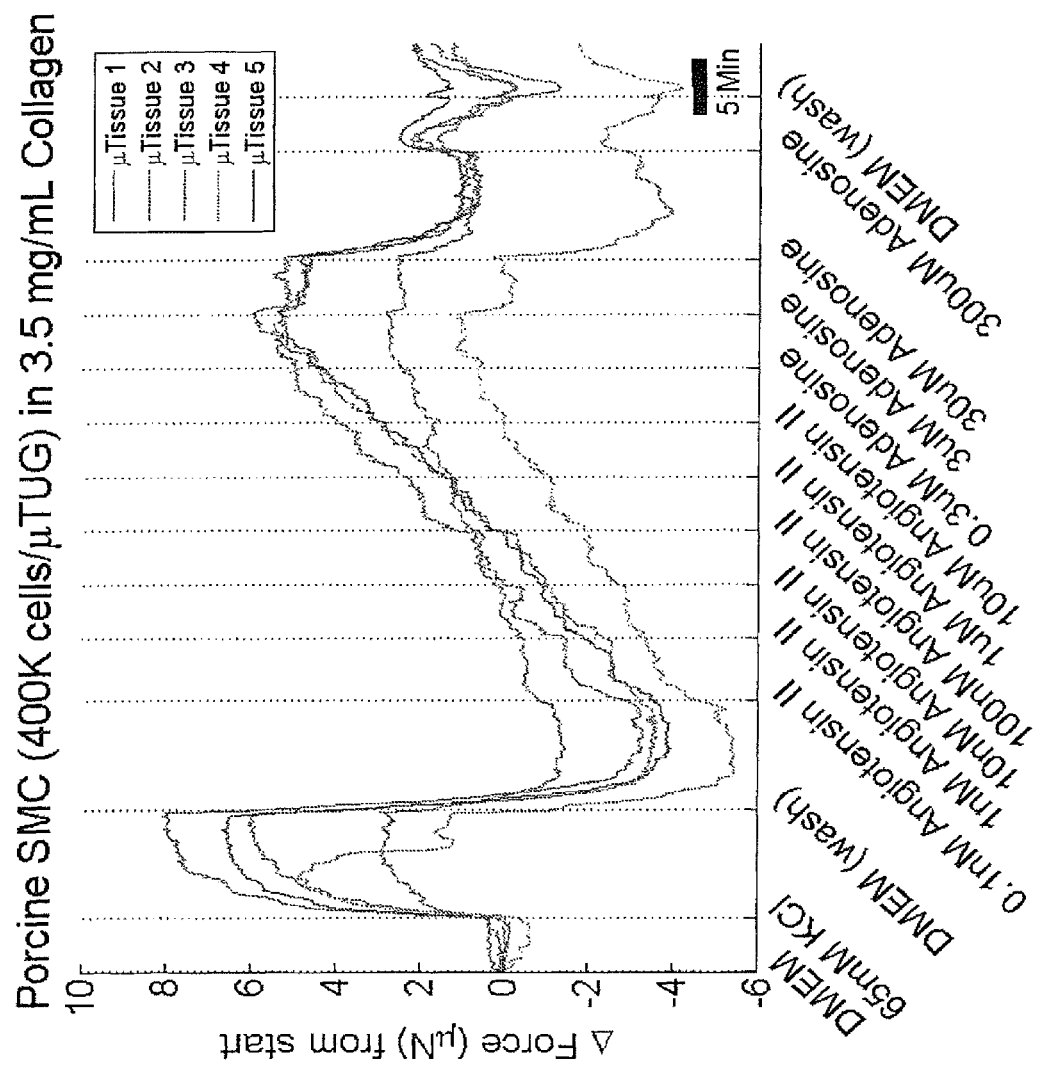

Additionally or alternatively, smooth muscle cells (e.g., isolated from pig cell) can be introduced into the devices. FIG. 14a and FIG. 14b provide exemplary graphs with traces showing contractile force evolution over time after exposure to compounds at different concentrations. For example, drugs can be introduced that are known to have effects on blood pressure (which can be controlled by smooth muscle cells constricting or relaxing to affect blood vessel diameter), and the affect of such compounds on the contractility of the tissues within the devices can be determined. Such techniques can be used in connection with the screening or other preclinical testing of compounds for the treatment of blood pressure.

The techniques disclosed herein can provide for the engineering of microtissues with desired contractile characteristics. For example, the reactive force of the posts can impose a mechanical preload on each construct. Elastic boundaries can enhance the development of the sarcoplasmic reticulum in cardiomyocytes, resulting in higher cell tension, as evidenced by the large forces generated by CMTs tethered to the posts. This high cell tension can lead to a strongly compacted extracellular matrix, an increased alignment of the cells and a better development of the sarcomeric structures, resulting in a higher cross-sectional stress generated by the tissue.

Substrate stiffness can regulate cardiac function. For example, following a myocardial infarction, beating cardiomyocytes can be replaced by a fibrotic scar (E≈35-70 kPa) that can be several-fold stiffer than normal myocardium (E≈5-15 kPa) and spontaneous contractions, cytoskeletal organization or differentiation of cardiomyocytes can be influenced by such change in stiffness. The density of 3D collagen/fibrin matrix can feedback to increase contractile forces of cardiac cells embedded within it. Simultaneously, the matrix composition can have a direct impact on the ability of the cells to reorganize within the matrix and to remodel it. Thus, a denser matrix can be less compacted by the cells, and can result in a poor alignment of the cells and a lower efficiency of the cardiac tissue, characterized by the generated cross-sectional stress. Electrical stimulation can induce a better compaction of the matrix by the cells and a faster alignment of the cells, improving the cell coupling. By forcing the CMTs to beat periodically over days, electrical stimulation can also increase the positive effect of the auxotonic load due to the stiff cantilevers and can lead to higher cross-sectional stress. The combination of electrical stimulation and auxotonic load thus appears to improve both the structure and the function of the CMTs while demonstrating the importance of biomechanical cues as regulators of myocardial structure and function.

Moreover, the techniques disclosed herein can provide a microtissue assay suitable for high throughput monitoring of, e.g., drug-induced changes in spontaneous frequency of contractility in CMTs. The micrometer scale of the CMTs can provide for rapid penetration of soluble effectors into the constructs. For example, introduction of isoproterenol and/or digoxin can produce reproducible, dose-dependent effects on microtissue contractility and beating frequency.

In certain embodiments, replacement of 10% horse serum with physiological growth factors such as insulin-like growth factor (IGF-1), triiodothyroxine (T3) and the steroid agonist clenburerol can further improve the diastolic relaxation and contractile reserve of human CMTs. Productive seeding routines, cantilever stiffness and electrical conditioning routines can be employed in connection therewith. The effects of growth factors implicated in physiological growth can be systematically assessed both individually and in combination. For each of the growth factors assessed, dose-response relationship can be determined.

In connection with the techniques disclosed herein, the structural and functional characteristics of CMTs can be similar to in vivo heart muscle, and can provide for high throughput, low volume screening applications. Moreover, techniques disclosed herein can quantitatively demonstrate the impact of physical parameters on the maturation, structure and function of cardiac tissue provide opportunities to elucidate mechanisms of load-dependent myocardial remodeling in stable, three-dimensional, working muscle preparations. Furthermore, the techniques disclosed herein can provide for reproducible contractile phenotyping, which can be difficult in two-dimensional culture models.

In one aspect of the disclosed subject matter, the microfabricated tissues gauges disclosed herein can be used to measure certain parameters of the microtissues generated therein. These parameters can include, for example, one or more of static force, dynamic force, stresses, cross-section, alignment, calcium signaling, beat frequency, or the like. As used herein, static force can be the resting force generated by the microtissues (cardiac and/or non-cardiac). Dynamic force can be, in the context of cardiac microtissue, the systole force minus the diastole force (i.e., static force). Alternatively, dynamic force be the change in force due to the addition of one or more compounds that alter the contractility of the microtissue. For example, addition of epinephrine can cause a change in force. Stresses can be calculated by dividing the total force by the cross-sectional area of the micro-tissue. Since the cross-sectional area can vary along the length of the micro-tissue, the stress can also vary. Alignment can refer to the orientation and elongation of the cells and the orientation of the ECM fibers. Calcium signaling can measured by using calcium-sensitive dyes such as Fluo-4. Beat frequency can refer to how often a microtissue oscillates in its contractile state. This is exemplified in cardiac microtissues. A field-stimulator can be used to measure the maximum capture rate which, i.e., the maximum beating frequency at which a tissue can be electrically paced. Likewise, electrical stimulation can be used to determine the force-frequency response describing the relationship between the magnitude of force and beating frequency.

For purposes of illustration, and not limitation, description will now be made of techniques for measurement of parameters of micro-tissues within the devices described above with reference to FIG. 7

One aspect of cardiac function is the ability of these cells to integrate into an electromechanically coupled multicellular unit and generate substantial static ('diastolic') and peak dynamic ('systolic') forces during contraction. In one embodiment, the force exerted by the microtissues 755 within the µTUGs can be determined by measuring a displacement of each cantilever 750$a$ and 750$b$ (collectively 750) (e.g., the displacement of each cap). Each microcantilever's spring constant can be calculated utilizing a capacitive MEMS force sensor mounted on a micromanipulator according to known methods, and/or can be estimated computationally based on geometric dimensions of the cantilevers along with known values for the Young's modulus of the material of the cantilevers, e.g., PDMS.

An imaging device can acquire image data of the microcantilevers. For example, as noted above, the caps of the micro-cantilevers 750 can include one or more fluorescent emitters. An imaging array, such as a CCD, emCCD array, or CMOS chip can be used to detect the fluorescent response of the emitters to determine the position of the cap. Alternatively, as noted above, the caps can be patterned with identifiable geometric characteristics and can be imaged optically. The imaging device can be configured to generate an image at a particular frequency, e.g., 20 Hz, and each image can be processed to determine the position of the micro-cantilevers over time. The displacement of fluorescent micro-beads over time due to the contractions of the cardiac microtissue 755 can be processed, over time, so as to quantify microtissue forces based on the known spring constants of the micro-cantilevers.

For example, in a relaxed state 710, the cardiac microtissue 755 can a force on the micro-cantilevers 750 such that the distance between each cantilever is $L_{ref}$ 760. When contracted 720, the cardiac microtissue 755 can exert a greater force on the micro-cantilevers 750 such that distance between each cantilever decreases to L 765. The tension, F, exerted by the microtissue 755 can be determined as $F=k(L_{ref}-L)$, where k is the spring constant of the micro-cantilevers. Moreover, the cross-sectional stress, σ, of the microtissue 755 can be determined as $\sigma=4F/\pi ab$, where a is the cross sectional length of the microtissue 755 in a relaxed state and b is the cross sectional length of the microtissue 755 in a contracted state.

Figure 7:
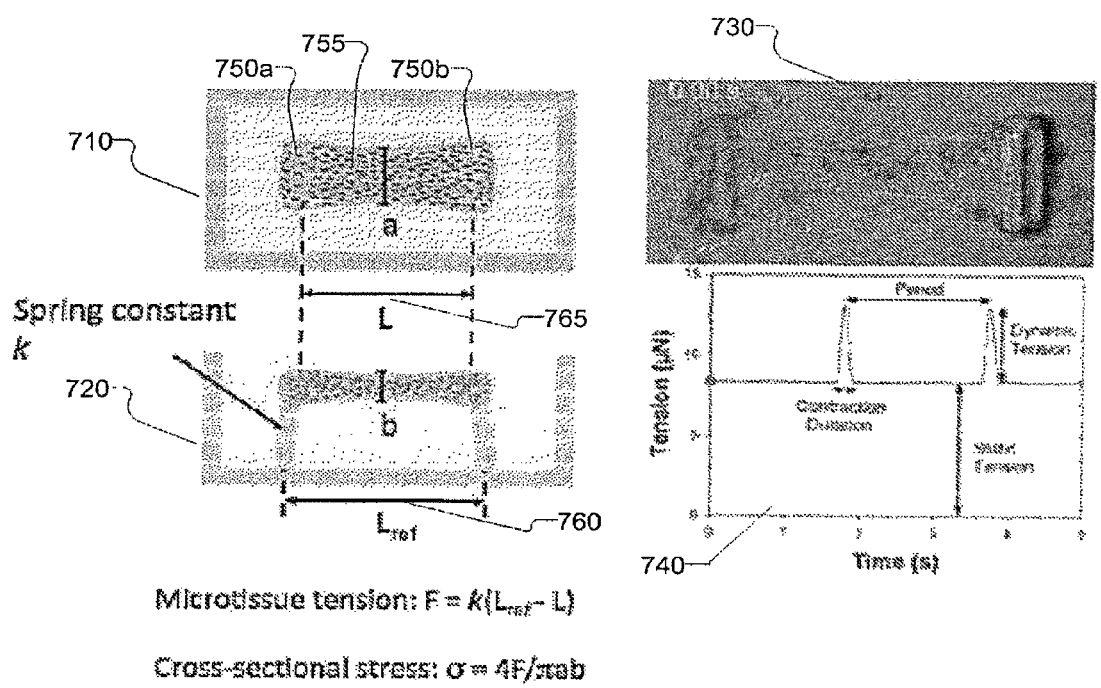
FIG. 7 is a diagram illustrating techniques for characterization of physiological parameters of microtissues in accordance with an embodiment of the disclosed subject matter.
Figure 8:
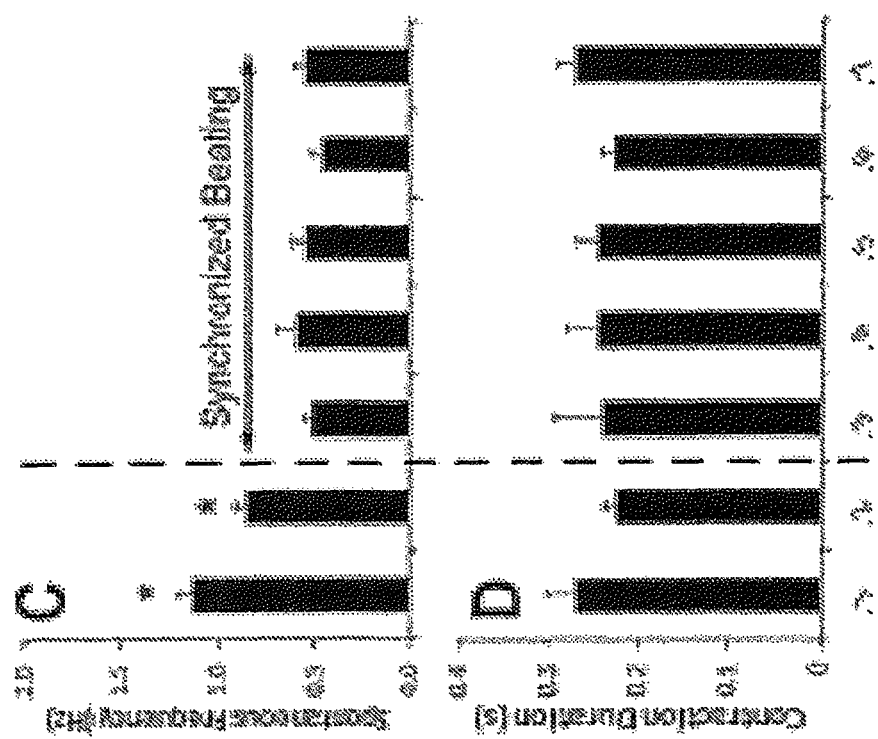
FIG. 8 illustrates exemplary graphs of spontaneous beat frequency and contraction duration of cardiac microtissues in accordance with an embodiment of the disclosed subject matter.
Figure 9:
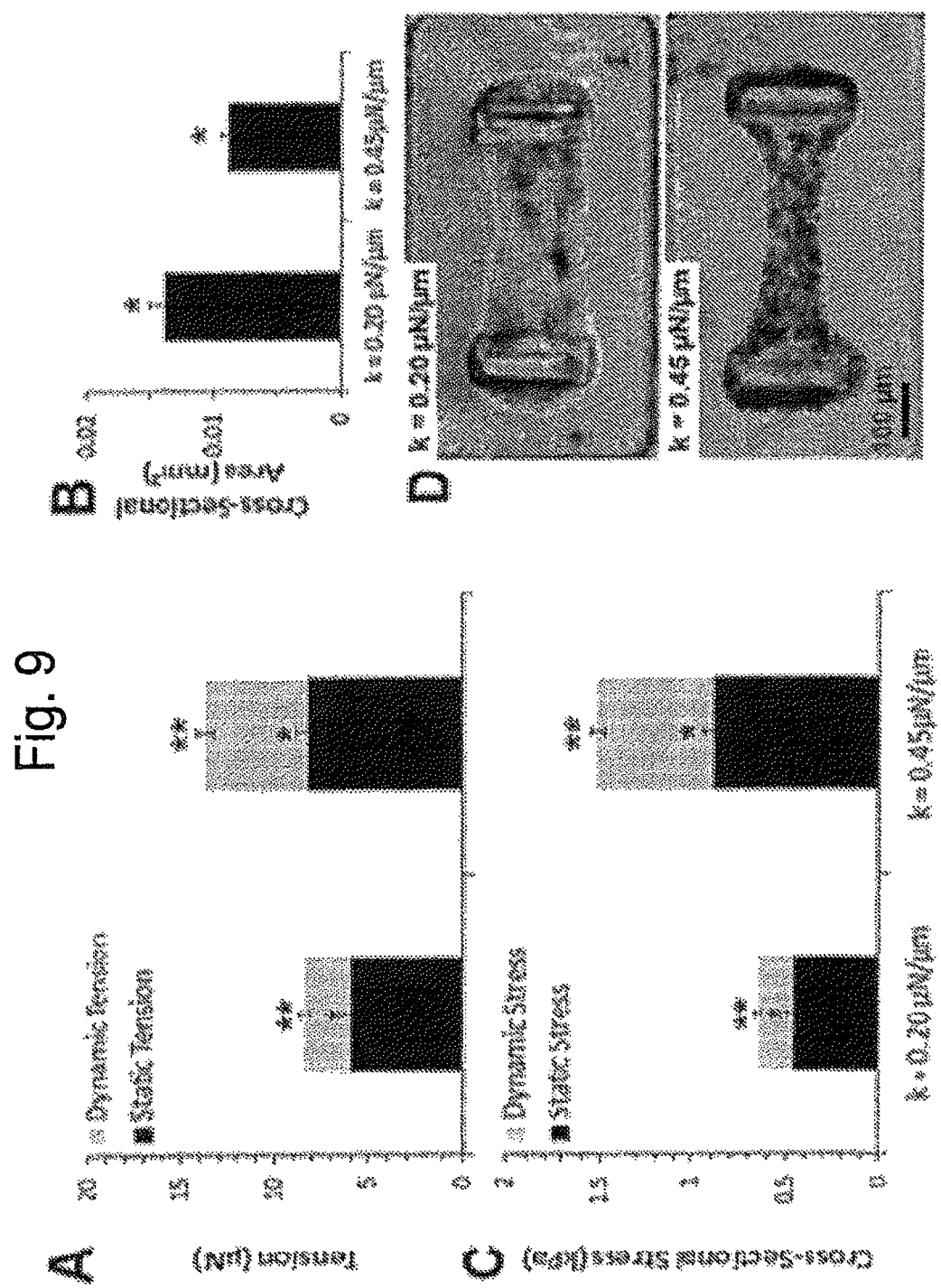
FIG. 9 illustrates the effect of post stiffness on dynamic and static contractility of cardiac microtissues in accordance with an embodiment of the disclosed subject matter.
Figure 10:
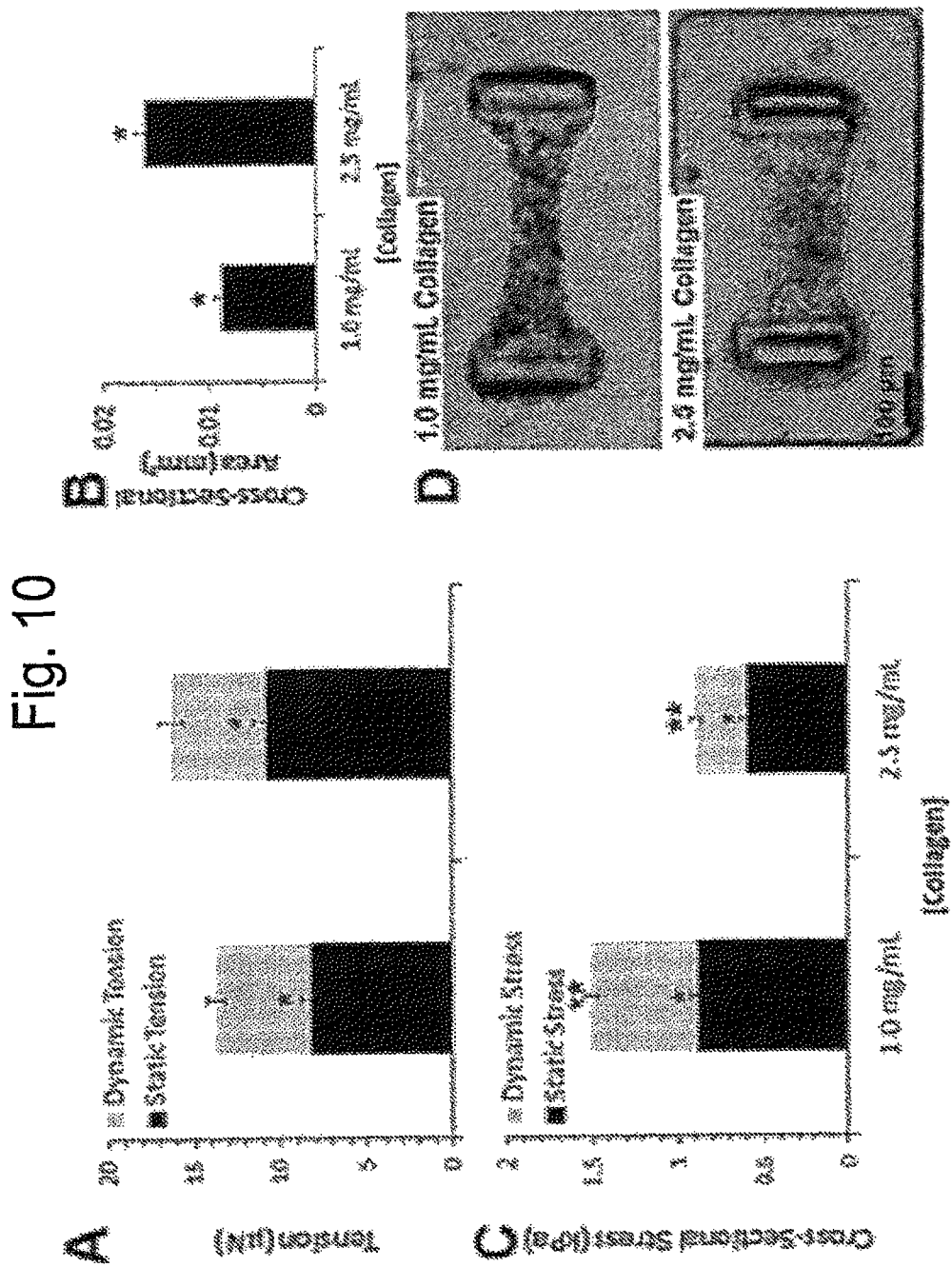
FIG. 10 illustrates the effect of matrix composition on dynamic and static contractility of cardiac microtissues in accordance with an embodiment of the disclosed subject matter.
Figure 11:
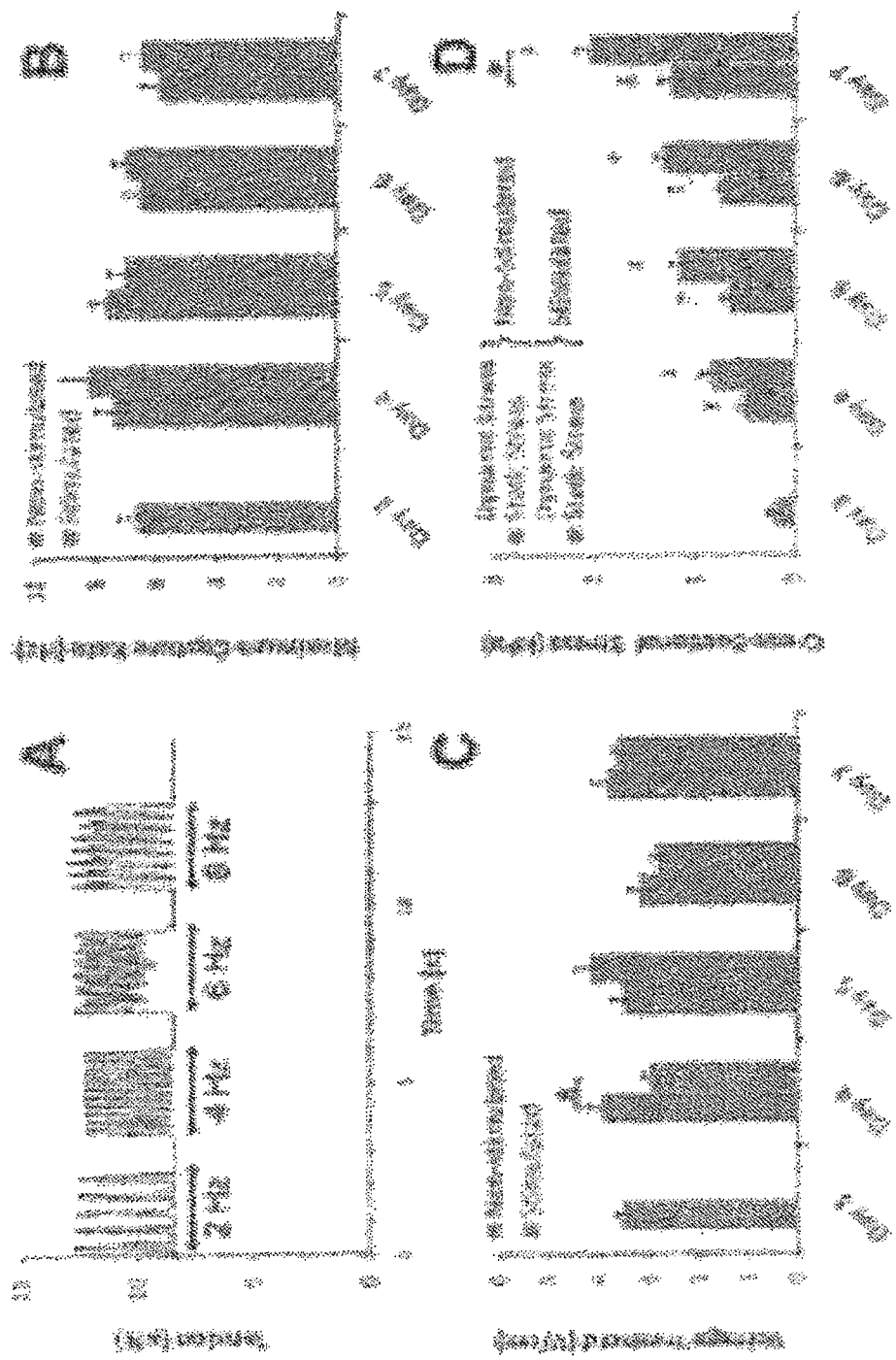
FIG. 11 illustrates functional properties of non-stimulated and electrically stimulated cardiac microtissues in accordance with one embodiment of the disclosed subject matter.
Figure 12:
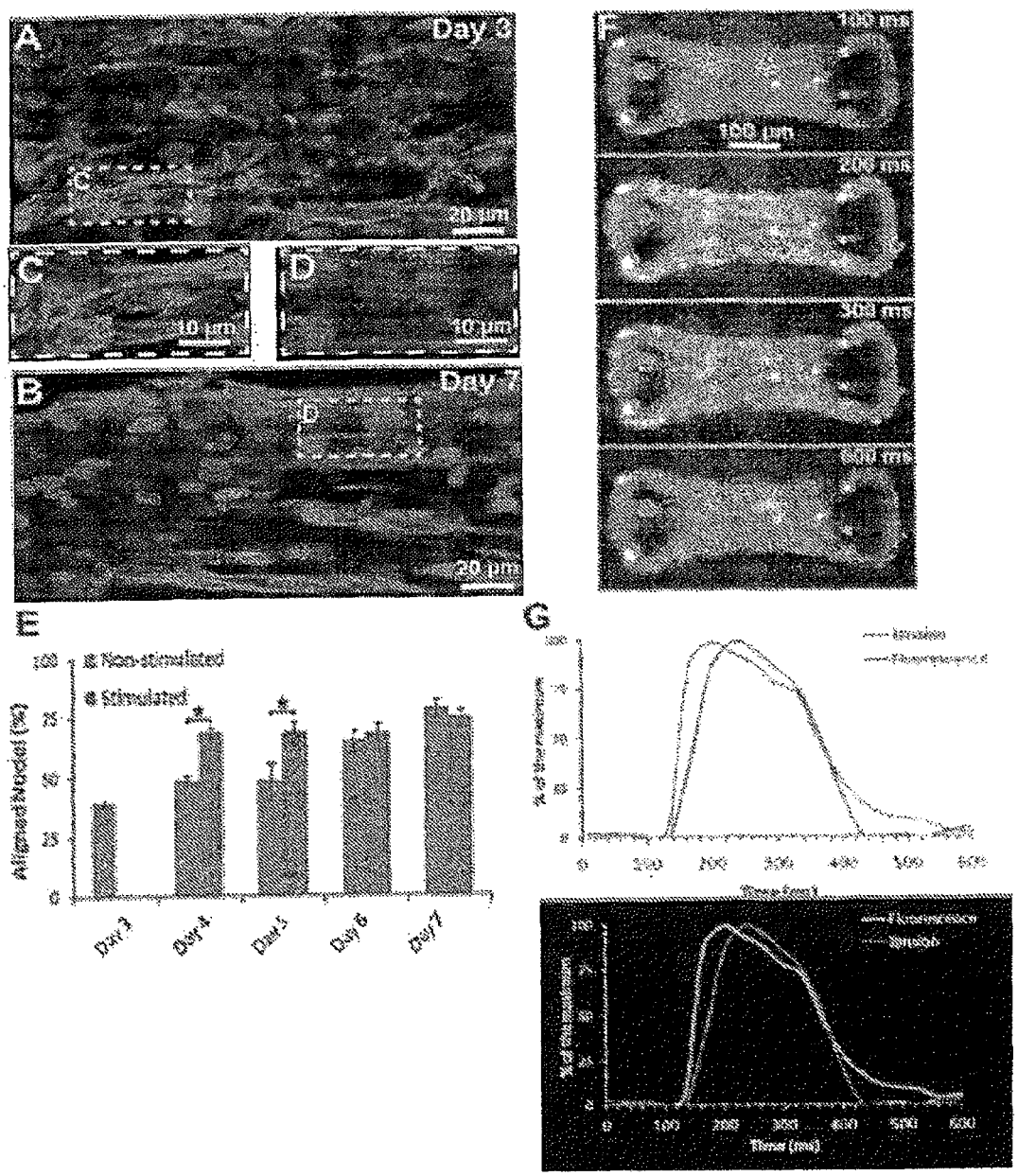
FIG. 12 illustrates structural properties and calcium signaling of cardiac microtissues in accordance with one embodiment of the disclosed subject matter.

FIG. 7 depicts an image 730 of an exemplary microtissue coupled to two micro-cantilevers. Additionally, an exemplary graph 740 of the tension of the microtissue 755 over time is provided. As shown in the graph, the force exerted by the microtissue 755 can be decoupled into two forces, e.g., static tension and dynamic tension. Static tension can be the baseline force exerted on the micro-micro-cantilevers 750 due to the anchoring of the microtissue 755. With each beat of the microtissue 755, an additional force (e.g., dynamic force) can be applied for the contraction duration. Thus, the total force exert can equal the static force plus the dynamic force as a function of time. Moreover, the beat frequency can be calculated from the change in dynamic frequency over time.

In an exemplary and non-limiting embodiment, deflections that can be measured according to the techniques disclosed herein can range from approximately 0.1 μm to 50 μm. The spring constant of the micropillars can be 0.45 μN/μm, but can be decreased to 0.2 μN/μm. For 0.45 uN/um, the range of measurable forces can be 0.045 μN to 22.5 μN per micropillar, or 0.09 μN to 45 μN for two micropillars. For 0.2 μN/μm, the range of measurable forces can be 0.02 μN to 10 μN per micropillar, or 0.04 μN to 20 μN for two micropillars.

In one embodiment, the alignment of cells within the microtissue within a μTUG can be determined. For example, the cells can be immunostained and imaged using an imaging device, and the image can be processed to determine alignment of the cells. In one exemplary embodiment, the microtissues can be incubated with antibodies against troponin T and detected with fluorophore-conjugated, isotype-specific, anti-IgG antibodies and counterstained. Alignment can be quantified from DAPI images by fitting ellipses. Nuclei of the cells can be considered aligned, for example, when the angle between their long axis and the axis joining the cantilevers was less than 20 degrees.

In one embodiment, the structural properties of the microtissues within the μTUGs can be determined in connection with calcium signaling. For example, the CMTs can be exposed to a fluorescence-based calcium indicator and fluorescent images can be taken. The periodic calcium release in the cells within the CMTs can be observed. Moreover, synchronization of calcium release throughout the CMT can also be observed. In certain embodiments, the calcium release can be synchronized with coherent beating and the maturation of the CMTs, and can be associated with the development of sarcomeric structures. Thus, in certain embodiments, structural characteristics of the CMTs can be determined with reference to the detected calcium release.

Moreover, electrical characteristics of the CMTs can be determined while simultaneously measuring forces and determining the structural characteristics of the CMTs. For example, electrical characterization of the CMTs can be used in connection with drug screening. In certain embodiments, calcium release can herald the depolarization of the CMTs, and the calcium concentration can be measured using fluorescent dies (e.g., fluo-3), the fluorescent response of which can correspond to the concentration of calcium existing the extracellular matrix. However, one of ordinary skill in the art will appreciate that known techniques for determining the electrical characteristics of CMTs can be employed in connection with the techniques disclosed herein. The techniques disclosed herein can provide efficient and high throughput assays that can simultaneously characterize both the structural and electrical properties of the CMTs with the use of a single platform, and thus can obviate the need for separate efforts to characterize electrical characteristics and structural characteristics.

In one embodiment, the effect of length-tension effects on the microtissues within the μTUGs can be determined. For example, the μTUGs can be stretched owing to their elastomer construction. The techniques described herein to characterize the forces, alignment, and/or other structural properties of the microtissues can be used in connection with the stretching of the μTUGs to determine the effect of stretching on the microtissues. Because force generation in muscle can be affected by resting length of the muscle, this assay can provide a measure of the physiology and health of the tissue.

In one embodiment, the μTUGs disclosed herein can be used in connection with in-vitro drug testing using pharmacological agonists. For example, isoproterenol and forskolin can be examples of the utility of human CMTs as a screening platform for inotropic agents. Doxorubicin and quinidine can be examples of the utility of human CMTs for toxicity screening. Moreover, in certain embodiments, the dose-response of the CMTs, including a contractility response to the dose, of compounds including isoproterenol and dioxin can be measured. One of ordinary skill in the art will appreciate that a variety of compounds can be introduced to the CMTs, and need not be limited to those disclosed herein.

Moreover, as disclosed herein, the μTUGs can be used in connection with the identification of compounds that modulate the contractility of tissues generated in the devices, and/or determining an effect of a known compound on the contractility of one or more tissues. For example, the effect of a known pharmacologic agent on patient-specific cells and/or cells of different lineages can be determined. Additionally, the techniques disclosed herein can include measuring the effect of compounds and/or environmental factors on populations of cells (e.g., a class of individuals or patients, such as "diabetic obese smokers"). The compounds can include, but are not limited to, small molecule pharmaceuticals, biologics, siRNA, bodily fluid such as blood serum, or any other organic or inorganic compound. Furthermore, in certain embodiments, the effect of an environmental factor on the contractile function of the microtissues can be determined. The environmental factors can include, but are not limited to, gravity, hypoxia, pressure, magnetic field, smoke, and/or the presence of nanoparticles. For example, the extracellular matrix can be adapted to replicate in vivo environmental characteristics, such as those observed in connection with starvation. The effect of such environmental characteristics on the contractility of the tissues can be determined in vitro in accordance with the disclosed subject matter.

While creating human CMTs with typical physiological, pathological and pharmacological responses of adult human myocardium can be accomplished with the techniques disclosed herein, a platform for preclinical target validation and drug screening can also reflect the genetic diversity of human myocardium. The importance of genetic determinants can be illustrated by the numerous rare (<$1/1,000$ patients) mutations that cause inherited hypertrophic and/or dilated cardiomyopathies. However, more frequent (>$1/20$ patients) genetic polymorphisms can substantially affect disease risk, disease severity or treatment response in patients with cardiovascular disease. In one embodiment, epicardial fat can be one suitable somatic tissue for iPSC reprogramming due to efficiency of iPSC generation with adipose tissue relative to fibroblasts.

While IGF-1, T3 and clenbuterol can promote physiological myocardial hypertrophy as occurs during normal growth or exercise, other agonists like angiotensin II (AngII), endothelin (ET-1) and phenylephrine (Phe) can be associated with pathological hypertrophy, as associated with heart failure or hypertension. Accordingly, the functional, morphological and molecular effects of the pathological hypertrophy mediators to establish in vitro models of disease can be likewise examined in accordance with the techniques disclosed herein. Such in vitro models of physiological cardiac hypertrophy and pathological cardiac hypertrophy can enable inspection of the distinct mechanisms of these conditions in human myocardium and can permit screens for small molecules or other agents that might selectively inhibit pathological myocardial hypertrophy or promote physiological hypertrophy. Complementary cell-type specific assessments including markers of fibroblast activation (e.g., secreted collagen, α-smooth muscle actin expression), markers of myocyte damage (e.g., troponin, apoptosis) and reporters of physiological versus pathological hypertrophy (e.g., Akt versus NFAT activation) can provide additional mechanistic clarity.

In certain embodiments, electrical stimulation, as described above, can be used in connection with the techniques disclosed herein. Electrical stimulation can induce compaction of the matrix by the cells, a faster alignment of the cells, and can increase the positive effect of the auxotonic load due to the stiff cantilevers and can lead to higher cross-sectional stress. Moreover, electrodes can also be used to measure electrical activity (e.g., current or voltage) to provide maximum capture rate, the effect of pacing, and/or force-frequency response. Biophysical parameters can also be assessed, including a) spontaneous rate, b) resting tension, c) peak active tension, and d) maximum capture rate by external pacing with an electric field and the force-frequency slope at these rates.

Figure 16:
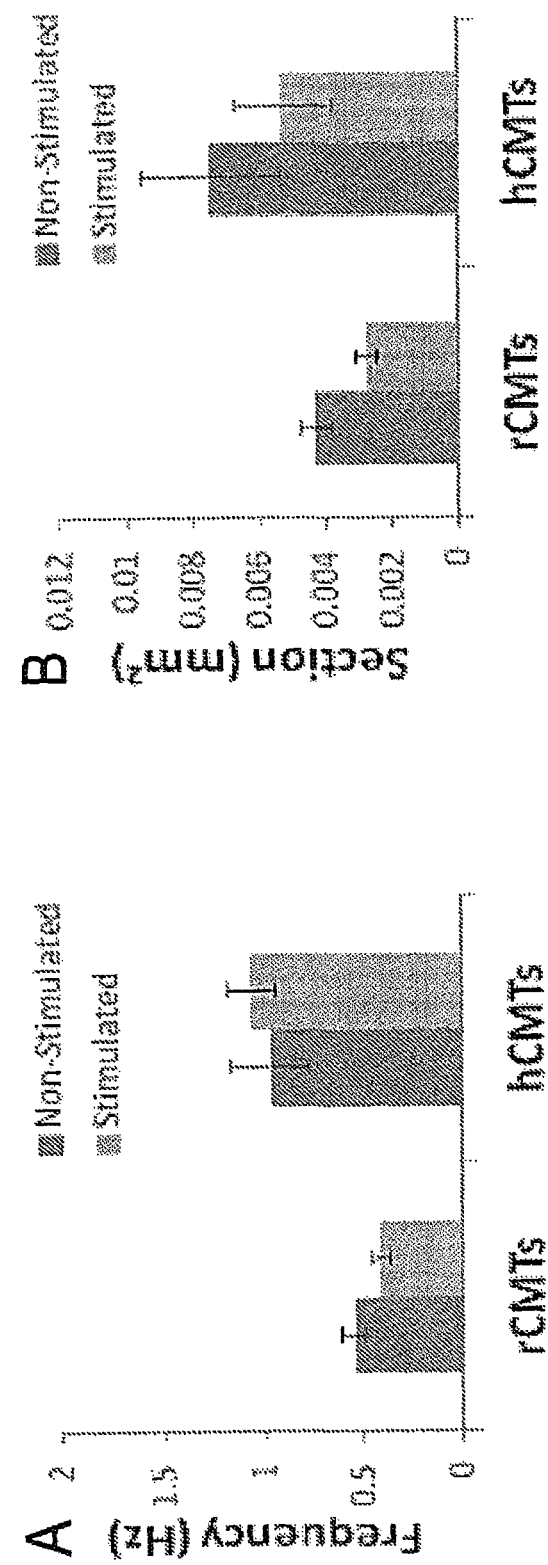
FIG. 16 illustrates the effect of electrical stimulation on neonatal rate cardiac microtissues and human cardiac microtissues in accordance with one embodiment of the disclosed subject matter.

For purposes of illustration and not limitation, FIG. 16 illustrates a modulation in beat frequency and in cross-sectional area of both neonatal rat CMTs ("rCMTs") and human CMTs microtissues generated in accordance with the disclosed subject matter when electrically stimulated. For example, FIG. 16A illustrates the beat frequency of rCMTs and hCMTs without electrical stimulation and with electrical stimulation. As is evident from the figure, beat frequency for the rCMTs decreased with electrical stimulation, and beat frequency for hCMTs increased with electrical stimulation. FIG. 16B illustrates the cross-sectional area of rCMTs and hCMTs with electrical stimulation and without electrical stimulation. As shown, the cross sectional area decreases for both rCMTs and hCMTs with electrical stimulation.

Additionally, for purposes of illustration and not limitation, FIG. 15 depicts an exemplary plot of dynamic tension (i.e., the tension due to contractile forces of the CMTs) over time under the presence of electrical stimulation. From this plot beat frequency can be derived. Electrical stimulation can be applied to modulate the beat frequency, and in certain embodiments can be applied across a plurality of μTUGs to synchronize beat frequency.

In certain embodiment a combination of one or more of the techniques disclosed herein can be employed in connection with each other. Such techniques can include but are not limited to, for example, modulating the matrix and post mechanics to affect cellular responses; controlling cellular assembly into multicellular structures with desired geometries or structures; modeling human tissue, tissue mechanics, tissue development, damage, repair, or regeneration; integrating the devices with other devices or sensors on an experimental platform to examine organ-organ interactions; generating force, motion, pumping electrical activity, and/or communication of signals; and or testing for toxic effects in environmental monitoring.

Additionally or alternatively, the techniques described above in connection with determining physiological parameters of the CMTs (e.g., static force, dynamic force, stresses, cross-section, alignment, calcium signaling, and/or beat frequency) can be used in connection with the techniques disclosed above in connection with drug screening. For example, the techniques disclosed herein can enable the characterization and/or determination of the effect of a compound on the physiological parameters of the CMTs. Owing to the structural similarities of the CMTs to in vitro tissues, such techniques can provide preclinical characterization closely resembling that experienced in vitro.

For purposes of illustration, one assay in accordance with the subject matter disclosed herein can include observing how microtissues change as a result of electrical stimulation (or how this change might be affected by a compound). Similarly, the change in contractile response on a stiffer versus softer cantilever is can be observed, and likewise how a compound or manipulation like siRNA impacts that change. Assembling cells into a microtissue can itself induce cells to behave in a more predictive manner relative to what occurs in vivo, and therefore any other assays (nonmechanical) that would be performed on these cells while in this microtissue format, can also be performed. For example, measuring proliferation rates, motility, gene expression, protein expression, receptor kinetics, cellular signaling, biochemical activity, kinase activity, second messenger levels, metabolism, cell suicide, or differentiation, and the change in these measures to compounds, siRNA, environmental perturbations can be measured and/or observed. Furthermore, in certain embodiments, whether the tissues actually form a band of cells and a matrix that spans the microcantilevers, whether cells generate force in a synchronized manner, whether the tissues remain attached or break and fail, are also measurements that can be made in accordance with the subject matter disclosed herein, and how drugs impact these different phenomena can be assayed.

In certain embodiments, CMT development can be assessed through additional functional, structural and molecular readouts. β-adrenergic contractile reserve can be examined with an isoproterenol dose-response ($10^{-9}$, $10^{-8}$, $10^{-7}$, $10^{-6}$, $10^{-5}$). Histological methods can be used to quantitatively evaluate myocyte size, the degree of nuclear alignment with the long axis, and the extracellular matrix as a fraction of total area (should be <10%) in addition to qualitative assessments of striations and overall myocyte density. Complementary biochemical phenotyping can probe the CMTs for evidence of apoptosis (based on caspase activation), tissue damage (based on cardiac troponin in medium) and extracellular matrix turnover (based on aminoterminal propeptide of Type 1 collagen [PINP] and Type I collagen telopeptide [ICTP] in medium.

In one embodiment, with freshly explanted human heart tissue, a collagenase-based digestion can be used to obtain large amounts (e.g., >$10^7$ cells) of stromal vascular fraction (SVF) cells from >30 grams of epicardial fat present in all human hearts. Cardiac fibroblasts and cardiac myocytes can also be obtained using perfusion-based, collagenase digestion protocols. Multiple routines for iPSC induction can be employed including 4-factor induction using non-viral minicircle DNA vectors or miRNA-mediated induction using miR302/367. Comparisons can be made on the basis of efficiency in generating iPSCs using criteria, for example: 1) pluripotent stem cell morphology and unlimited self-renewal, 2) expression of pluripotency markers and down-regulation of differentiation markers, 3) reprogramming factor independence, and 4) proof of functional differentiation through the highest stringency test possible. The fourth criteria can be addressed by determining if contracting CMTs can be derived from the resulting iPSC colonies. Accordingly, further comparisons can be made on the basis of the time required for new myocyte differentiation, the ability to generate >95% pure populations of immature myocytes (based on SIRPA and cTnI). Tissue formation efficiency and physiological responses typical of human CMTs can also be compared.

The absence of dystrophin expression in patients with Duchenne muscular dystrophy can produce both skeletal muscle myopathy and cardiomyopathy. In dystrophin-deficient mice, designed to model Duchenne muscular dystrophy, exhibit myocardial contractile defects and profound contraction-induced damage following isoproterenol stimulation in vivo or in vitro. Harvesting somatic cells from genotyped patients with cardiomyopathy due to Duchenne muscular dystrophy and their non-affected family members can be performed. iPSC lines can be derived and CMT arrays can be created with myocytes differentiated from these patient-specific iPSC lines. Somatic cells from well-characterized patients with Duchenne muscular dystrophy can be provided. Using a method of generating patient-specific myocytes and culture conditions, multiple sets of patient-specific CMTs can be created for each case of Duchenne muscular dystrophy and their respective controls without muscular dystrophy.

Examination of both intra-patient and inter-patient differences can establish the validity and robustness of patient-specific CMTs as disease models. Intra-patient variability can be examined at multiple levels in the process by comparing multiple lines of iPSCs from each patient, multiple myocyte populations from each iPSC line and multiple CMTs from each myocyte population. These intra-patient comparisons can be based on gene expression and methylation profiles by RT-PCR and based on CMT function and morphometry. Inter-patient comparisons can be based on contractility, passive (diastolic) stiffness, contractile reserve and morphological features of the CMTs to under standard conditions. Dystrophin expression can be measured (by RT-PCR) and histological methods can be used to quantitatively evaluate myocyte size, the degree of nuclear alignment with the long axis, and the extracellular matrix as a fraction of total area. Functional and morphologic parameters can be examined after conditions of agonist-induced stress (isoproterenol $10^{-7}$, $10^{-6}$, $10^{-5}$) and following acute increases in biomechanical stress induced by acute stretch protocols designed to increase diastolic CMT length by 10 percent (this will increase both preload and afterload.

In certain embodiments, the μTUGs disclosed herein can be coupled to or incorporated into microfluidics devices. For example, the μTUGs can be integrated with "human-on-a-chip" devices, and can include multiple compartments connected by one or more channels. Cells of one or more organs can be housed in each compartment. The channels can be coupled to, e.g., a pump, and can be configured for the introduction of one or more microfluidic streams that deliver, remove, or exchange fluids bathing the wells/microwells. Such devices can apply motions involved in, e.g., the beating of a heart, the expansion of the lungs, or the peristalsis of the intestines. Such devices can automate the delivery of compounds and media to each compartment separately in an automated fashion.

As embodied herein, the presence of the cantilevers can constrain the manner in which the microtissues contract, align, and organize in the microwells, and can impact multicellular organization and structure. These structural effects can influence the phenotype of the cells within such constructs, sometimes triggering the cells to behave more physiologically or behave more pathologically, and in either case in a manner more similar to the in vivo setting than sometimes can be attainable in traditional culture on planar substrates. As such, using these devices as a platform to support cell culture can be broadly useful for modeling certain disease, healing, and physiologic processes.

Because all cells can generate mechanical forces against their surroundings, and use these forces both to impact extracellular and intracellular structures as well as to drive cellular signaling through a process known as mechanotransduction, methods to measure, perturb, or otherwise study these forces can have many utilities. The ability to measure the mechanical forces that cells generate within a microtissue, and control the mechanical conditions within microtissues, can be used for many applications. For example, muscle tissues such as cardiac tissue, skeletal muscle, and smooth muscle all generate forces as part of their primary function. Compounds in the pharmaceutical industry are constantly being developed to enhance or suppress contractile activity in these tissues, or often to avoid the side effects of impacting these critical tissues. Methods to measure this contractile behavior is thus desired. In the area of stem cell therapy and regenerative medicine, in connection with the subject matter disclosed herein, protocols can isolate, purify, or induce the most therapeutically beneficial contractile cardiac cells for use in clinical therapies. The techniques disclosed herein can be used to assess which cell sources and differentiation/culture protocols would give rise to the best cells for such uses. Beyond muscle physiology, contractile forces generated by many other cell types are also associated with physiology and disease. For example, fibroblasts differentiate into myofibroblasts to generate large contractile forces within stiff tissues leading to scarring and fibrosis. Forming microtissues containing these cells in accordance with the disclosed subject matter can provide a platform for screening new compounds or gene targets that could interrupt their contractile function and thus the scarring process. Contractile activity can be critical for morphogenesis in early development, so microtissues formed from such cells could be used to screen for compounds that would impact their contractility and likely act as teratogens. Contractile activity of premalignant tumor cells can impact tumor progression and thus tumor microtissues could be used to screen for compounds to target such tumors. Contractile activity can be critical for cell motility and thus microtissues could be used to identify compounds that modulate immune cell trafficking. One of ordinary skill in the art will appreciate that the exemplary uses disclosed herein are not intended to be limiting, and that the disclosed subject matter is applicable to many uses for the microtissues.

EXAMPLE

The disclosed subject matter is further described by examples, presented below, with reference to FIGS. 8-13.

The use of such examples is illustrative only and in no way limits the scope and meaning of the disclosed subject matter or of any exemplified term.

In a first example, cardiomyocytes were isolated from 0-1 day neonatal Sprague Dawley rat pups by a Trypsin digestion protocol as previously described. The resulting cell population was immediately subjected to CMT generation. CMTs were cultured in high glucose DMEM (Mediatech, Inc.) containing 10% horse serum (Invitrogen), 2% chick embryo extract (Charles River Laboratories International, Inc.), 4 mM L-glutamine, 1 mM sodium pyruvate, 100 units/mL penicillin, and 100 mg/mL streptomycin (all from Invitrogen). Cell culture medium was changed every day. Stock solution of Isoproterenol (Sigma-Aldrich) of 10 mM was made in MilliQ water and stock solution of Digoxin (GlaxoSmithKline) of 10 mM was made in DMSO. Calcium staining was obtained by incubating CMTs for 1 h with the acetoxymethyl ester of fluo-3 (fluo-3/(AM), Invitrogen) as a fluorescent dye at 2 µM in PBS with 0.02% of Pluronic F127 (BASF).

SU-8 masters were fabricated following a modified version of the technique described previously. Layers of SU-8 photoresist (Microchem) were patterned onto a silicon wafers by successive spin coat, alignment, exposure and bake steps. PDMS (Sylgard 184, Corning) µTUG substrates were molded from the SU-8 masters as described above with an additional step of embedding fluorescent microbeads (Fluoresbrite 17147, Polysciences Inc.) into the cantilevers to accommodate computerized cantilever deflection tracking. PDMS stamps were submerged in ethanol and treated in an ultrasonic pen cleaner (Model 600, Rotex Co.) to displace air trapped in the inverted pattern. After 5 minutes, the stamps were transferred into the wells of a six-well plate and 10 ml of ethanol and fluorescent bead solution (3000:1) was added to each well. The six-well plates containing stamps were then centrifuged for 1 minute at 1000 rpm to settle the fluorescent beads into the pattern on the stamps. The ethanol was then allowed to evaporate overnight at room temperature, leaving the beads behind covering the entire patterned surface. PDMS molds were then cast onto the stamps to produce the final µTUG substrates. As a result, the fluorescent beads covering the stamp were embedded in the surface of the substrates.

Cantilever spring constants were calculated utilizing a capacitive MEMS force sensor mounted on a micromanipulator as described previously. Images of the sensor tip and cantilever head were acquired during each test using an Olympus FV1000 confocal microscope with an air immersion 0.4 NA 10× objective. To account for local deformation of the PDMS material around the sensor, the spring constant of the MEMS sensor was calibrated against the side of the PDMS well which can be viewed as an elastic half space of the same material modulus as the PDMS cantilevers and was found to be 104 nN/µm±1.9 nN/µm. This value was then used for the subsequent measurements of the force required for cantilever bending. For each measurement the sensor tip was placed 20 microns below the top of the post and the probe translated laterally against the outer edge of the cantilever using a custom written Lab View (National Instruments) script. The probe base was displaced approximately 150 microns for each measurement. The displacement of the probe tip (and thus of the cantilever head) was calculated from the spring constant measured above and the reported sensor force and was verified visually during the deformation. 5 cantilevers were measured across a substrate and measurements were repeated for three different substrates of each condition. Cantilevers were found to have linear responses up to approximately 30 microns of deformation, beyond which the response became non-linear. As the cantilever deformations observed in this paper were all below 30 microns, this section was fit using a linear fit. The spring constant of the rigid and flexible cantilevers across a substrate were found to be 0.45 µN/µm±0.10 µN/µm and 0.20 µN/µm±0.03 µN/µm, respectively.

Before cell seeding, the PDMS templates were sterilized in 70% ethanol followed by UV irradiation for 15 min and treated with 0.2% Pluronic F127 for 60 min to reduce cell adhesion. A reconstitution mixture, consisting of 1 mg/mL or 2.5 mg/mL liquid neutralized collagen I from rat tail (BO Biosciences) and 0.5 mg/mL fibrinogen from bovine plasma (Sigma-Aldrich), was then added to the surface of the substrates on ice and templates were degassed under vacuum to remove bubbles in the liquid. A cooled suspension of half a million cells within reconstitution mixture was then added to the substrate and the entire assembly was centrifuged to drive the cells into the micropatterned wells, resulting in around 500 cells per well. Excess collagen/fibrinogen and cells were removed by de-wetting the surface of the substrate before incubating at 37° C. to induce collagen polymerization. The appropriate media was then added to each substrate. By using a live/dead cell viability assay (Invitrogen), cell viability over time was estimated. The average ratio of living cells after seeding in the µTUGs of 64±9%, was statistically similar to the viability right after isolation (69±11%), and slowly decreased to 46±13% after 7 days of culture.

For quantifying microtissue forces, brightfield and fluorescence images were taken at 20 Hz within each template, using a Photometrics Evolve EMCCOcamera (Photometrics), and an A-Plan 10× objective on a Nikon Eclipse Ti (Nikon Instruments Inc.) equipped with a live cell incubator. Only tissues that were uniformly anchored to the tips of the cantilevers were included in the analysis. The displacement of fluorescent micro-beads at the top of the cantilevers was then tracked with using the SpotTracker plug-in in ImageJ (National Institutes of Health).

In one example, electrical stimulation was started 3 days after cell seeding, by placing two carbon electrodes (¼ in diameter; Ladd Research Industries) on the sides of the samples (separated by 2 cm), connected through platinum wires to a stimulator as described previously. Voltage threshold is the minimum voltage at which the CMTs are observed to beat synchronously under electrical field stimulation at 1 Hz using 1 ms square biphasic pulses. Maximum capture rate is defined as the maximum pacing frequency for synchronous contractions at ~20% over voltage threshold. Continuous stimulation was achieved by using biphasic square pulses of 1 ms at 6V/cm and 0.2 Hz.

In one example, microtissues were fixed with 4% paraformaldehyde in PBS, permeabilized with 0.2% Triton X-100 in PBS, incubated with antibodies against troponin T (Thermo Scientific) and detected with fluorophore-conjugated, isotype-specific, anti-IgG antibodies and counterstained with DAPI (Invitrogen). Alignment was quantified from DAPI images by fitting ellipses with Image J. Nuclei were considered aligned when the angle between their long axis and the x-axis (the axis joining the two cantilevers) was inferior less than 20°. Cross-sectional areas were estimated from z-stack images obtained with a 40× water-immersion objective attached to a laser scanning microscope Zeiss LSM 510 (Carl Zeiss Inc.).

Figure 5:
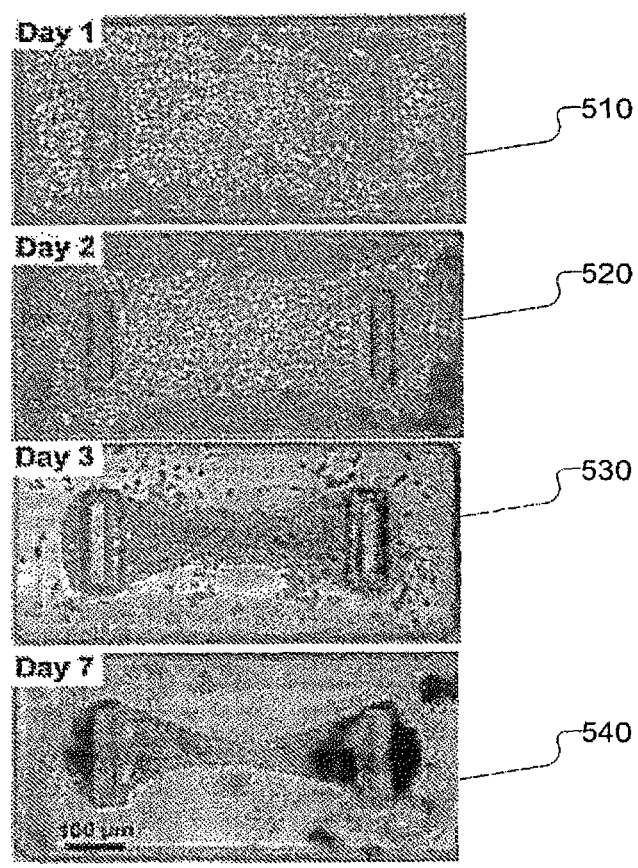
FIG. 5 is a series of images of the generation of microtissues in accordance with an embodiment of the disclosed subject matter.

To generate microscale constructs of cardiac cells within collagen/fibrin 3D matrices, arrays of wells within a PDMS mold where microfabricated. The mold was immersed in a suspension of cells and reconstitution mixture (liquid neutralized collagen I and fibrinogen) and the entire assembly was centrifuged to drive the cells into the micropatterned wells. Excess collagen/fibrinogen and cells were removed and the remaining constructs were polymerized. Over time of cultivation, the cells spread inside the matrix, formed cell-cell contacts, and spontaneously compacted the matrix over several days (FIG. 5). Two T-shaped cantilevers incorporated within each template anchored the contracting matrix, constraining the contraction of the collagen/fibrin matrix to form a linear band that spanned across the top of the pair of cantilevers. This resulted in a large array of CMTs anchored to the tips of the cantilevers per substrate. The spring constant of each cantilever was controlled by altering the ratio between PDMS and curing agent. Linear bending theory and experimental measurements were used to report the load-displacement relationship for 2 different ratios PDMS/curing agent, leading to measured spring constants of 0.45 µN/µm and 0.20 µN/µm. These spring constants were then used to link the measured cantilever deflections to the amount of force generated by CMTs.

After cell seeding, at day 0, the collagen/fibrin matrix contained evenly distributed amorphous round heart cells (FIG. 5). Over time, cells elongated, aligned along the axis between the cantilevers, and started to beat as single cells at day 1 to 2 at a spontaneous frequency of 1.1±0.1 Hz. Remodeling and compaction of the matrix led to a slower and coherent beating, rhythmically deflecting the posts at 0.5±0.1 Hz after day 3 (FIG. 8C), and to a marked reduction of construct size (final diameter 50 to 70 µm at the thinnest portion of the construct at day 7). The beating frequency was slower than the beat rate of an intact adult rat heart (5-7 Hz) or a neonatal rat heart (4-6 Hz) but close to frequencies measured in centimeter scale cardiac tissues generated from isolated cardiomyocytes. Over time of cultivation, the total contraction duration (contraction and relaxation) appeared to be roughly stable around 0.25±0.01 s (FIG. 8D), similar to contraction durations measured in centimeter scale cardiac tissues.

The spring constant of the cantilevers impacted both the dynamic and the static tension generated by cells. The dynamic tension, as used herein, is defined as the force exerted during contractile beatings of CMTs and owing from the cardiomyocytes whereas the static tension can be due to the baseline tonic traction of all the cells that leads to the compaction of the matrix. By staining for troponin-T, it was determined that the native cell isolate contained 58±3% cardiac myocytes; native myocardium can consist of multiple cell types, including cardiomyocytes and up to 50% of non-myocytes (fibroblasts and endothelial cells), which can be actively involved in cross talk. Beating contractions of CMTs tethered to flexible cantilevers (k=0.20 µN/µm) at day 5 generated 2.39±0.24 µN whereas CMTs tethered to more rigid cantilevers (k=0.45 µN/µm) generated two-fold more force (FIG. 9A). The static tension was also lower between flexible cantilevers than CMTs between rigid cantilevers but the relative impact was less substantial (6.03±0.36 vs. 8.25±0.61 µN, respectively). The lower contractility of CMTs tethered to flexible cantilevers appeared to result in decreased compaction of the collagen/fibrin matrix by the cells (FIG. 9B), resulting in 3.4-fold lower dynamic cross-sectional stress (i.e. tension normalized by the cross-sectional area) and 2-fold lower static cross-sectional stress at day 5 (FIG. 9C-D). These cross-sectional stresses can be lower than those measured in intact heart muscle or in centimeter-scale engineered tissues.

In addition to the cantilever stiffness, the influence of the bulk modulus of the collagen/fibrin matrix on the contractility of simulated CMTs was examined. It was observed that the static tensions increased when the collagen density was increased from 1.0 mg/mL to 2.5 mg/mL (FIG. 10A). However, this higher static tension in CMTs constructed from 2.5 mg/ml collagen was not sufficient to overcome the increased rigidity of the denser collagen matrix (FIG. 10B), thus leading to less matrix remodeling and lower values of both dynamic and static stress (FIG. 10C-D).

In one example, two parallel carbon electrodes were inserted on both sides of the arrays and to stimulate simultaneously arrays of CMTs (FIG. 11A). Electrical stimulation (biphasic pulses, 6V/cm, 0.2 Hz, 1 ms) was initiated 3 days after cell seeding and maintained until day 7. The functionality of CMTs was estimated every day by three parameters: voltage threshold (VT), maximum capture rate (MCR) and cross-sectional stress. VT and MCR were found to be stable over days and similar for non-stimulated (VT=3.6±0.1 V/cm and MCR=7.0±0.3 Hz) and stimulated CMTs (VT=3.5±0.1 V/cm and MCR=7.2±0.3 Hz) (FIG. 11B-C). The obtained VT and MCR values are slightly higher than those measured previously, which may be explained by the use of non-enriched cardiac cells in this non-limiting example. It was observed that continuous electrical stimulation tended to accelerate the generation of higher dynamic contraction stress (587±61 Pa vs. 419±69 Pa at day 4, after 24 h of stimulation) and to increase the generated static stress (almost 2-fold higher at day 7 after 4 days of stimulation) (FIG. 11D). The cell alignment was quantified by staining cell nuclei before measuring their orientation (FIG. 12A-E). 75% of the nuclei were aligned along the CMT long axis at day 4 in the case of stimulated CMTS, after only 24 h of stimulation, whereas non-stimulated CMTs reach this level of organization after 6 days of culture (FIG. 12E). Thus, electrical stimulation can provide cardiomyocytes with maturation signals.

It was also examined whether electrical signals conduct across the engineered tissues by exposing constructs to a fluorescence-based calcium indicator and taking fluorescence images at 30 Hz. Spontaneous, periodic calcium release was observed in cells within the CMTs, but, synchronized calcium release across the entire microtissue were also observed (FIG. 12F). Both the fluorescence level within the tissue and the displacement of the pillars was measured. Examining time traces of calcium release and tension exerted by the tissue, the two profiles had a similar shape, with the measured tension slightly phase-delayed compared to the calcium release (FIG. 12G). This synchronized calcium release was observed with coherent beating and the maturation of the CMTs after approximately 3 days of culture, and was associated with the development of sarcomeric structures (FIG. 12A-E). Immuno-staining of CMTs initially showed initial almost random network of troponin-T positive cardiac myocytes at day 3 (FIG. 12A-B) that longitudinally aligned and elongated, with well developed parallel sarcomeric structures after 7 days of culture (FIG. 12C-D).

Figure 13:
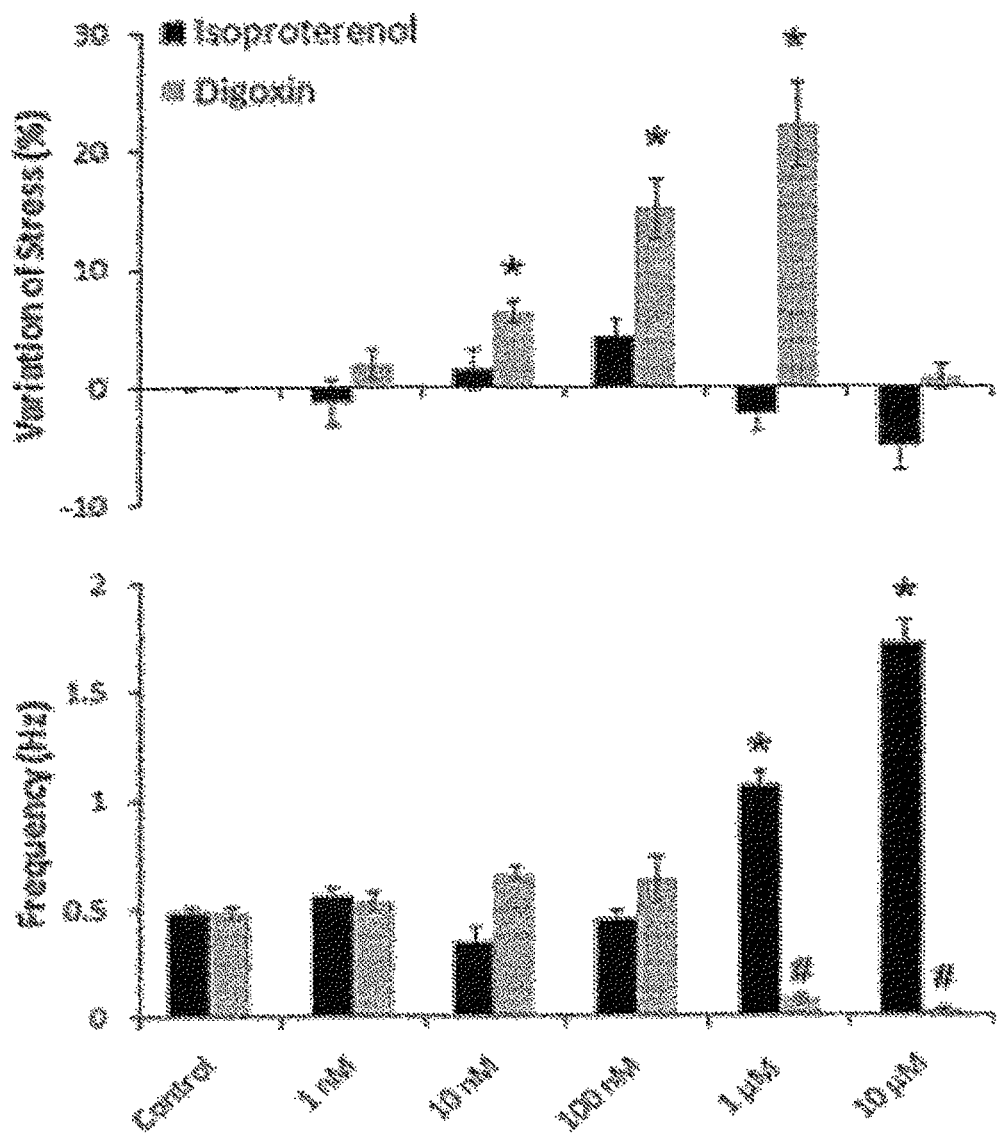
FIG. 13 illustrates effects of isoproterenol and digoxin on functionality of cardiac microtissues in accordance with one embodiment of the disclosed subject matter.

In one example, it was also examined whether CMTs responded appropriately to two cardiac compounds, isoproterenol and digoxin. To study the dose-response of the CMTs to these compounds, their concentrations were varied from 1 nM to 10 µM and the dynamic stress and the spontaneous frequency of CMTs were measured after 1 h (FIG. 13). Isoproterenol can be used as a β-adrenergic agonist with a positive chronotropic effect whereas digoxin is a cardiac glycoside that inhibits $Na^+/K^+$-ATPase (sodium pump), activates sarcoplasmic reticulum Ca2+-release channels and induces positive inotropic effects. Isoproterenol had no observable effect at 1 nM, a slight positive inotropic action (increase in contractility) at 10 and 100 nM and a slight negative inotropic effect (decrease in contractility) at 1 and 10 nM. In contrast, isoproterenol had an observed positive chronotropic action at 1 and 10 μM, doubling the spontaneous frequency at 1 μM and tripling it at 10 μM. Digoxin led to a positive inotropic response between 1 nM and 1 μM, with a maximal stress increase of 22±4% at 1 μM. At 10 μM, digoxin appears to be cardiotoxic with almost no inotropic effect but a strong negative chronotropic effect with a spontaneous frequency dropping under 0.04±0.01 Hz.

The presently disclosed subject matter is not to be limited in scope by the specific embodiments herein. Indeed, various modifications of the disclosed subject matter in addition to those described herein will become apparent to those skilled in the art from the foregoing description and the accompanying figures. Such modifications are intended to fall within the scope of the appended claims.

The invention claimed is:

1. A method for generating microtissues, comprising:
providing a micro-fabricated platform including at least one micro-well including a plurality of micro-cantilevers coupled to the bottom surface of each of at least one micro-well, each micro-cantilever including a cap at a terminal end thereof, wherein each of at least one micro-well is surrounded by a plurality of ridges;
immersing the platform in a suspension of cells;
driving the suspension of cells into the at least one micro-well;
de-wetting the ridges to remove excess suspension, thereby isolating the suspension of cells in each of at least one micro-well;
polymerizing the suspension to form a matrix;
cultivating the cells over time, to spontaneously compact the matrix, wherein the micro-cantilevers anchor the contracting matrix, constraining the contraction of the matrix to form a band of microtissue that spans across the micro-cantilevers; and
measuring a contractile function of the band of microtissue, wherein measuring comprises:
imaging the micro-fabricated platform, over time, to acquire image data determining a force exerted on the micro-cantilevers based on at least the image data and a spring constant corresponding to each micro-cantilever; and identifying a contractile function of the band of microtissue based on at least the determined force, wherein the contractile function includes one or more of beat frequency, contraction duration, change in beat frequency over time, change in contraction duration over time, or variance in any of these parameters.

2. The method of claim 1, wherein the suspension of cells includes a reconstitution mixture or a prepolymer.

3. The method of claim 2, wherein the reconstitution mixture includes collagen and fibrinogen.

4. The method of claim 1, wherein the suspension of cells includes neonatal rat heart cells.

5. The method of claim 1, wherein the suspension of cells comprises human cells.

6. The method of claim 1, wherein the suspension of cells includes human iPSC-derived cardiomyocytes.

7. The method of claim 1, wherein the suspension of cells includes one or more of heart cells, muscle cells, liver cells, neural cells, mesodermal, ectodermal, or endodermal lineage, embryonic or adult stem cells, fibroblasts, endothelial cells, smooth muscle cells of any origin, skeletal muscle cells, cardiac myocytes, myofibroblasts, epithelial cells, neuronal cells, glial cells, astrocytes, hepatocytes, kidney epithelial cells, intestinal cells, lymphocytes, or leukocytes.

8. The method of claim 1, wherein the suspension of cells includes one or more of cells of human origin or cells of non-human origin including mouse cells, rat cells, rabbit cells, pig cells, bovine cells, primate cells, non-mammalian cells, fish cells, insect cells, mold cells, dictostelium cells, worm cells, or *drosophila* cells.

9. The method of claim 1, wherein the suspension of cells includes one or more of cancer cells, non-eukaryotic cells, bacteria, or viruses.

10. The method of claim 1, wherein providing a micro-fabricated platform including at least one micro-well further comprises providing a micro-fabricated platform including a plurality of micro-wells.

11. The method of claim 10, wherein at least a first of the plurality of micro-wells includes cells from a first population, and at least a second of the plurality of micro-wells includes cells from a second population.

12. The method of claim 11, further comprising detecting a difference between the identified contractile function of the band of microtissue from the first of the plurality of micro-wells and the band of microtissue from the second of the plurality of micro-wells.

13. The method of claim 12, wherein the first population of cells, second population of cells, or both first and second population of cells are cultivated in a plurality of micro-wells each with a population of micro-cantilevers of a different stiffness, each with a matrix of a different composition, each with a band of microtissue electrically stimulated with a different frequency, or each with a combination thereof.

14. The method of claim 10, wherein at least a first of the plurality of micro-wells includes diseased cells, and at least a second of the plurality of micro-wells includes normal cells.

15. The method of claim 10, wherein at least a first of the plurality of micro-wells includes a first population of micro-cantilevers of a first stiffness and at least a second of the plurality of micro-wells includes a second population of micro-cantilevers of a second stiffness.

16. The method of claim 15, further comprising detecting a difference between the identified contractile function of the band of microtissue from the first of the plurality of micro-wells and the band of microtissue from the second of the plurality of micro-wells.

17. The method of claim 10, wherein at least a first of the plurality of micro-wells includes a matrix of a first composition and at least a second of the plurality of micro-wells includes a matrix of a second composition.

18. The method of claim 17, further comprising detecting a difference between the identified contractile function of the band of microtissue from the first of the plurality of micro-wells and the band of microtissue from the second of the plurality of micro-wells.

19. The method of claim 10, wherein at least a first of the plurality of micro-wells includes a band of microtissue electrically stimulated at a first frequency and at least a second of the plurality of micro-wells includes a band of microtissue electrically stimulated at a second frequency.

20. The method of claim 19, further comprising detecting a difference between the identified contractile function of the band of microtissue from the first of the plurality of micro-wells and the band of microtissue from the second of the plurality of micro-wells.

21. The method of claim 1, further comprising electrically stimulating the band of microtissue to thereby synchronize beating, if any, of the bands of microtissue of each of at least one micro-well.

22. The method of claim 21, comprising electrically stimulating the band of microtissue by oscillating at a frequency in a range of approximately 0.2 Hz to approximately 1 Hz.

23. The method of claim 21, comprising electrically stimulating the band of microtissue at 1, 2, or 3 Hz.

24. The method of claim 1, wherein the cap of each micro-cantilever includes one or more fluorescent emitters, and wherein imaging the micro-fabricated platform further includes imaging the fluorescent response of the one or more fluorescent emitters of each cap.

25. The method of claim 1, wherein measuring the contractile function further includes determining a static force and a dynamic force exerted on the micro-cantilevers over time based on at least the image data and the spring constant corresponding to each micro-cantilever.

26. The method of claim 25, further comprising measuring the level of calcium within the microtissue, wherein measuring includes:
  introducing one or more fluorescent dies into the microtissue; and
  imaging a fluorescent response of the fluorescent dies, over time, whereby the fluorescent response corresponds to a calcium concentration of the microtissues.

27. The method of claim 26, further comprising determining an electrical characteristic of the microtissue based on at least the calcium concentration of the microtissues, over time.

28. The method of claim 26, further comprising determining a delay between a release of calcium within the band of microtissue and the dynamic forces exerted by the microtissue.

29. The method of claim 1, further comprising identifying a compound that modulates the contractile function of the band of microtissue, wherein identifying the compound comprises:
  introducing the compound to the band of microtissue of at least one of the micro-wells;
  detecting a change in contractile function of the band of microtissue introduced to the compound over time.

30. The method of claim 29, further comprising cultivating the cells in a plurality of micro-wells each with a population of micro-cantilevers of a different stiffness, each with a matrix of a different composition, each with a band of microtissue electrically stimulated with a different frequency, or each with a combination thereof prior to detecting a change in contractile function of the band of microtissue introduced to the compound over time.

31. The method of claim 1, wherein the at least one micro-well includes a plurality of micro-wells, the method further comprising identifying a compound that modulates the contractile function of the band of microtissue, wherein identifying the compound comprises:
  introducing the compound to the band of microtissue of one of the plurality of micro-wells;
  detecting a difference between the identified contractile function of the band of microtissue introduced to the compound and a band of microtissue of another of the plurality of micro-wells.

32. The method of claim 31, wherein introducing the compound including introducing a pharmacologic agent to the band of microtissue.

33. The method of claim 31, wherein introducing the compound includes introducing one or more of a small-molecule pharmaceutical, a biologic, a siRNA, a bodily fluid, an organic compound, or an inorganic compound.

34. The method of claim 31, further comprising cultivating the cells in a plurality of micro-wells each with a population of micro-cantilevers of a different stiffness, each with a matrix of a different composition, each with a band of microtissue electrically stimulated with a different frequency, or each with a combination thereof prior to detecting a difference between the identified contractile function of the band of microtissue introduced to the compound and a band of microtissue of another of the plurality of micro-wells.

35. The method of claim 1, wherein the at least one micro-well includes a plurality of micro-wells, the method further comprising determining an effect of a compound on the contractile function of the band of microtissue, wherein determining the effect comprises:
  introducing the compound to the band of microtissue of one of the plurality of micro-wells;
  determining an effect on the contractile function of the band of microtissue introduced to the compound relative to a band of microtissue of another of the plurality of micro-wells.

36. The method of claim 35, wherein the one of the plurality of micro-wells includes a first band of microtissue of one of a first patient, a first region of tissue, a first species, or a first mixture of cell types, and wherein the band of microtissue of another of the plurality of micro-wells includes a second band of microtissue of one of a second patient, a second region of tissue, a second species, or a second mixture of cell types, and wherein determining an effect further comprises determining an effect on the contractile function of the first band of microtissue relative to the second band of microtissue.

37. The method of claim 1, further comprising determining an effect of an environmental factor on the contractile function of the band of microtissue, wherein determining the effect comprises:
  exposing the band of microtissue of one of the plurality of micro-wells to the environmental factor;
  determining an effect on the contractile function of the band of microtissue exposed to the environmental factor.

38. The method of claim 37, wherein the environmental factor includes one or more of gravity, hypoxia, pressure, magnetic field, smoke, or the presence of nanoparticles.

39. The method of claim 1, wherein the at least one micro-well includes a plurality of micro-wells, wherein a first of the plurality of micro-wells includes a first cell type and a second of the plurality of micro-wells includes a second cell type, the method further comprising identifying a difference in a viability metric between the first and second cell types.

40. The method of claim 1, further comprising measuring a structural characterization of the band of microtissue, the structural characterization including alpha-actinin periodicity, cell alignment, multicellular organization, cytoskeletal organization, cell-cell junction structure, extracellular matrix composition and structure, overall tissue shape, nuclear structure, number of cells per microtissue, distribution of cells within the microtissue, or proportion of cell types or source in the microtissue.

41. The method of claim 1, wherein each micro-cantilever is between 35 µm and 80 µm thick and less than 140 µm tall.

42. The method of claim 1, wherein each micro-cantilever is 45 µm thick, 100 µm wide, and 140 µm tall.

43. The method of claim 1, wherein the device is further adapted to provide for measurement of deflections of the micro-cantilevers of between 0.1 μm and 50 μm, and wherein the spring constant of each micro-cantilever is between 0.2 μN/μm and 0.45 μN/μm.

44. The method of claim 1, wherein the spring constant of each micro-cantilever is 0.45 μN/μm, and wherein the device is further adapted to provide for measurement of forces on the micro-cantilevers of between 0.045 μN and 22.5 μN for each micro-cantilever.

45. The method of claim 1, wherein the spring constant of each micro-cantilever is 0.2 μN/μm, and wherein the device is further adapted to provide for measurement of forces on the micro-cantilevers of between 0.02 μN and 10 μN for each micro-cantilever.

* * * * *

UNITED STATES PATENT AND TRADEMARK OFFICE
CERTIFICATE OF CORRECTION

PATENT NO.       : 9,512,396 B2
APPLICATION NO.  : 14/247951
DATED            : December 6, 2016
INVENTOR(S)      : Chen et al.

Page 1 of 1

It is certified that error appears in the above-identified patent and that said Letters Patent is hereby corrected as shown below:

In the Specification

STATEMENT OF FEDERALLY SPONSORED RESEARCH OR DEVELOPMENT:

Column 1 Line 19: delete "The invention was made with government support under grants EB00262 and EB08396, awarded by the National Institute of Biomedical Imaging and Bioengineering, and HL73305 and HL90747, awarded by National Heart, Lung, Blood Institute The government has certain rights in the invention." and insert -- "This invention was made with government support under grant number EB000262, EB008396, HL073305 & HL090747 awarded by the National Institutes of Health. The government has certain rights in the invention." --.

Signed and Sealed this
Twenty-fifth Day of April, 2017

Michelle K. Lee
*Director of the United States Patent and Trademark Office*